(12) United States Patent
Musumeci et al.

(10) Patent No.: US 9,862,710 B2
(45) Date of Patent: Jan. 9, 2018

(54) 1,2,4-OXADIAZOL COMPOUNDS ACTIVE AGAINST GRAM-POSITIVE PATHOGENS

(71) Applicants: I.E.ME.S.T—ISTITUTO EURO MEDITERRANEO DI SCIENZA E TECNOLOGIA, Palermo PA (IT); UNIVERSITÀ DEGLI STUDI DI MILANO-BICOCCA, Milan MI (IT)

(72) Inventors: Rosario Musumeci, Giarre (IT); Clementina Elvezia Anna Cocuzza, Milan (IT); Cosimo Gianluca Fortuna, Catania (IT); Andrea Pace, Palermo (IT); Antonio Palumbo Piccionello, Santa Flavia (IT)

(73) Assignees: ISTITUTO EURO MEDITERRANEO DI SCIENZA E TECNOLOGIA, Palermo (IT); UNIVERSITA' DEGLI STUDI DI MILANO—BICOCCA, Milan (IT)

( * ) Notice: Subject to any disclaimer, the term of this patent is extended or adjusted under 35 U.S.C. 154(b) by 0 days.

(21) Appl. No.: 13/839,485

(22) Filed: Mar. 15, 2013

(65) Prior Publication Data
US 2014/0275191 A1    Sep. 18, 2014

(51) Int. Cl.
*C07D 413/10*    (2006.01)
*C07D 413/14*    (2006.01)

(52) U.S. Cl.
CPC ......... *C07D 413/10* (2013.01); *C07D 413/14* (2013.01)

(58) Field of Classification Search
CPC .............. A61K 31/4245; C07D 271/06; C07D 413/10; C07D 413/14
USPC .......................................... 514/364; 548/131
See application file for complete search history.

(56) References Cited

U.S. PATENT DOCUMENTS

| 4,948,801 A | 8/1990 | Carlson et al. |
| 5,977,373 A | 11/1999 | Gadwood et al. |
| 2005/0043374 A1 | 2/2005 | Gravestock |

FOREIGN PATENT DOCUMENTS

| EP | 0352781 | 1/1990 |
| WO | 99/02525 | 1/1999 |
| WO | 03/035648 | 5/2003 |

OTHER PUBLICATIONS

Hauck, 2007, Bioorganic & Medicinal Chemistry Letters, vol. 17, p. 337-340.*
Fanni, search report for related IT application RM20130155, two pages (dated Jun. 2013).
Thomasco et al. "The synthesis and antibacterial activity of 1,3,4-thiadiazole phenyl oxazolidinone analogues" *Bioorganic & Medicinal Chemistry Letters* 13:4193-4196 (2003).

* cited by examiner

*Primary Examiner* — Rebecca Anderson
*Assistant Examiner* — Karen Cheng
(74) *Attorney, Agent, or Firm* — Nixon & Vanderhye PC

(57) ABSTRACT

The present invention relates to novel oxazolidinone compounds of general formula (I) having antibiotic activity also against multiresistant bacterial strains.

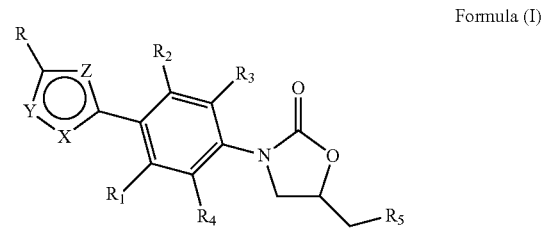

Formula (I)

25 Claims, 6 Drawing Sheets

SCHEME 1

SCHEME 2

SCHEME 3

1,2,4-OXADIAZOL COMPOUNDS ACTIVE AGAINST GRAM-POSITIVE PATHOGENS

SUMMARY

The present invention relates to novel oxazolidinone compounds of general formula (I) having antibiotic activity also against multiresistant bacterial strains.

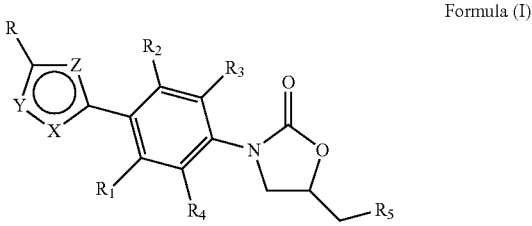

Formula (I)

STATE OF THE PRIOR ART

Use and misuse of antibacterial agents have resulted in the development of bacterial resistance to all antibiotics in clinical use irrespective of the chemical class or molecular target of the drug. Infections caused by multiresistant Gram-positive cocci, such as methicillin-resistant *Staphylococcus aureus* (MRSA), vancomycin-resistant enterococci (VRE) and penicillin-resistant *Streptococcus pneumoniae* (PNSSP), have emerged as major public health concern, both in hospital and community settings worldwide. The need for new antibiotics urged the Infectious Disease Society of America (IDSA) to issue the challenge to develop ten new antibiotics by 2020.

Oxazolidinones are a class of antibacterial agents which displayed activity against a variety of Gram-positive pathogens and are highly potent against multidrug-resistant bacteria. In particular, oxazolidinones are used to treat skin and respiratory tract infections caused by *Staphylococcus aureus* and streptococci strains, as well as being active against vancomycin-resistant *Enterococcus faecium*. Linezolid (FIG. 1), the first oxazolidinone antibiotic approved for clinical use, has been shown to inhibit translation at the initiation phase of protein synthesis in bacteria by binding to the 50S ribosomal subunit. Since 2001, however, linezolid resistance began to appear in *Staphylococcus aureus* and *Enterococcus faecium* clinical isolates and the rate of resistance raised especially among enterococci and *Staphylococcus epidermidis* strains with its usage.[1-4] In addition, linezolid therapy is not without side effects such as reversible myelosuppression and inhibition of monoamine oxidases (MAO).

A number of solutions to the problem of bacterial resistance are possible. Successful strategies include combination of existing antibacterial agents with other drugs as well as the development of improved diagnostic procedures that may lead to rapid identification of the causative pathogen and permit the use of antibacterial agents with a narrow spectrum of activity. Another strategy is the discovery of novel classes of antibacterial agents acting through new mechanisms of action. However, the most common approach, and still the most promising one, is the modification of existing classes of antibacterial agents to provide new analogues with improved activities, although activity and toxicity of the new analogues are not easily predictable.

In this context, many researchers have attempted to modify, without even obtaining results such as to lead to approval for use of new molecules, the structure of linezolid to improve the antibacterial activity. In order to rationalize the site of modifications, the structure of linezolid can formally be divided into four portions according to oxazolidinone antibacterials nomenclature[5]: i) the A-ring, consisting of the oxazolidinone central heterocycle; ii) the B-ring, consisting of a N-aryl moiety linked to the oxazolidinone nitrogen; iii) the C-ring, consisting of a carbo-heterocyclic functional group, not necessarily aromatic; iv) the side-chain, consisting of any functional group linked to the oxazolidinone C(5) or in an isosteric position with respect to an A-ring of general type (FIG. 1).

Figure 1

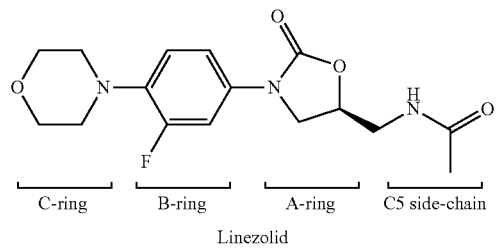

Linezolid

Different types of modifications are reported in literature; the most common one regards the C-ring, while only few modifications were reported for the A-ring, and in some cases good activity was retained.[6-7]

Our group previously reported that the replacement of the oxazolidinone (A-ring) with an isosteric 1,2,4-oxadiazole heteroaromatic ring resulted in a lack of activity.[8]

Therefore, these compounds have been chosen as references for inactive linezolid-like compounds in a virtual screening approach.

The purpose of the present invention is to find new molecules suitable as medicaments which exceed the limits and disadvantages of the prior art molecules, in terms of antibacterial activity, especially against resistant strains, and harmlessness.

SUMMARY OF THE INVENTION

The present invention is based on the discovery that the substitution of the C-ring of linezolid-like molecules, with a five-membered heterocyclic ring, also substituted, containing 2 or 3 heteroatoms, is effective for the obtainment of new antibiotic oxazolidinones with a tunable activity by the presence of further modifications at the B-ring and at the C(5) side-chain of the oxazolidinone nucleus.

Therefore, the object of the present invention are new compounds with a general formula (I), and their use for the treatment of infections caused by Gram-positive bacteria, Formula (I)

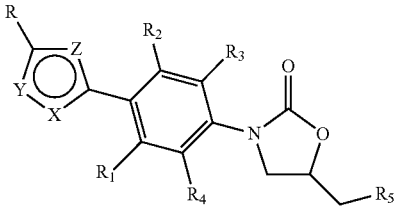

as racemic mixtures or pure enantiomers or mixtures enriched with either one of the S or R enantiomer
where:
X, Y, Z are independently: CH, O, N, S, with at least two heteroatoms;
R=H, F, Cl, Br, I, C1-C3 alkyl (methyl, ethyl, n-propyl, iso-propyl), C3-C6 cyclo-alkyl, aryl, hetero-aryl (thiophenyl, furanyl, pyridyl, pyrimidyl, pyridazinyl, pyrrolidinyl, piperidyl), $NH_2$, OH, SH, $NHR_6$, $N(R_6)_2$, $OR_6$ with $R_6$=C1-C3 alkyl, C3-C6 cyclo-alkyl, aryl, heteroaryl, C1-C4 acyl; $R_{1-4}$=independently H or F;
$R_5$=—$NH_2$; —I; —NCS; —OH; $N_3$; —$NHC(X)CH_3$ with X=O or S; —$NHC(X)CH_2Z$ with X=O, S, Z=F, Cl; —$NHC(X)CHZ_2$ with X=O, S, Z=F, Cl; —$NHC(X)CZ_3$ with X=O, S, Z=F, Cl; —$NHC(X)NHR_7$ with X=O, S, $R_7$=H, C1-C3 alkyl, C3-C6-cyclo-alkyl, (hetero)aryl, C1-C3-acyl or N-substituted azoles selected between pyrrole, pyrazole, imidazole, 1,2,3-triazole, 1,2,4-triazole.

In a preferred embodiment of the invention, new compounds present a general formula (II),

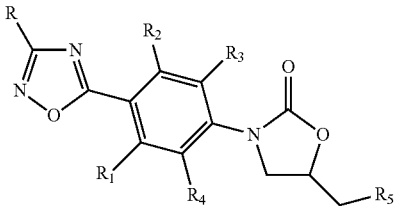

Formula (II)

as racemic mixtures or pure enantiomers or mixtures enriched with one of the S or R enantiomer
where:
R=H, F, Cl, Br, I, (C1-C3) alkyl (methyl, ethyl, n-propyl, iso-propyl), (C3-C6) cyclo-alkyl, aryl, heteroaryl, $NH_2$, OH, SH, $NHR_6$, $N(R_6)_2$, $OR_6$ with $R_6$=(C1-C3) alkyl, (C3-C6) cyclo-alkyl, aryl, heteroaryl, (C1-C4) acyl;
$R_{1-4}$=independently H or F;
$R_5$=—$NH_2$; —I; —$N_3$; —OH; —NCS; —$NHC(X)CH_3$ with X=O or S; —$NHC(X)CH_2Z$ with X=O, S, Z=F, Cl; —$NHC(X)CHZ_2$ with X=O, S, Z=F, Cl; —$NHC(X)CZ_3$ with X=O, S, Z=F, Cl; —$NHC(X)NHR_7$ with X=O, S, $R_7$=H, (C1-C3) alkyl, (C3-C6) cyclo-alkyl, aryl, heteroaryl, (C1-C3) acyl.

Specific embodiment of the invention consists on compounds with general formula (II) where R is methyl, ethyl, n-propyl, iso-propyl;
or compounds with general formula (II) where at least one between $R_1$, $R_2$, $R_3$ or $R_4$ is a fluorine atom, while the other are H;
or compounds with general formula (II) where $R_5$ is selected between: —NHC(=O)$CH_3$, —NHC(=S)$CH_3$, —NHC(=O)$CH_2F$, —NHC(=S)$CH_2F$, —NHC(=O)$CH_2Cl$, —NHC(=S)$CH_2Cl$, —NHC(=S)$NH_2$, NHC(=O)$NH_2$, —NHC(=O)NH$CH_3$, —NHC(=S)NH$CH_3$, —NHC(=O)NH$C_2H_5$, —NHC(=S)NH$C_2H_5$, —NCS; 1,2,3-triazol-1-yl;
or compounds with general formula (II) where R3 is a methyl and R5 is selected between: —NHC(=O)$CH_3$, —NHC(=S)$CH_3$, —NHC(=O)$CH_2F$, —NHC(=S)$CH_2F$, —NHC(=O)$CH_2Cl$, —NHC(=S)$CH_2Cl$, —NHC(=S)$NH_2$, NHC(=O)$NH_2$, —NHC(=O)NH$CH_3$, —NHC(=S)NH$CH_3$, —NHC(=O)NH$C_2H_5$, —NHC(=S)NHC2H5, —NCS; 1,2,3-triazol-1-yl;
or compounds with general formula (II) where R1 is F, R2, R3 and R4 are H and R3 is a methyl and R5 is selected between: —NHC(=O)$CH_3$, —NHC(=S)$CH_3$, —NHC(=O)$CH_2F$, —NHC(=S)$CH_2F$, —NHC(=O)$CH_2Cl$, —NHC(=S)$CH_2Cl$, —NHC(=S)$NH_2$, NHC(=O)$NH_2$, —NHC(=O)NH$CH_3$, —NHC(=S)NH$CH_3$, —NHC(=O)NH$C_2H_5$, —NHC(=S)NH$C_2H_5$, —NCS; 1,2,3 triazol-1-yl.

In a preferred embodiment of the invention, all compounds indicated above are pure S enantiomer or in a mixture enriched with the S enantiomer.

In a further embodiment of the invention the claimed compounds are intended for use in the treatment of infections caused by Gram-positive bacteria, preferably multi-antibiotic resistant (also called multi-resistant), for example in the treatment of infections caused by *Staphylococcus* spp, *Enterococcus* spp, *Streptococcus* spp, in particular of infection caused by *Staphylococcus aureus, Staphylococcus epidermidis, Staphylococcus hominis, Enterococcus faecium, Enterococcus faecalis, Streptococcus pneumoniae*. Especially if resistant to one or more of the antibiotics methicillin, vancomycin, penicillin, macrolides, fluoroquinolones and linezolid.

A second object of the invention are pharmaceutical compositions comprising the compounds of the invention as active ingredients and a pharmaceutically acceptable excipient.

Such compositions are intended for use in the treatment of infections by Gram-positive bacteria including multi-resistant strains.

A third object of the invention are processes for preparing the compounds of the invention which comprises the steps shown in diagrams 1, 2 and 3.

In one embodiment of the invention the methods comprise one or more steps of separation of the enantiomers S and R or enrichment of the racemic mixture in one of the enantiomers, preferably the S enantiomer.

A fourth object of the invention are processes for the preparation of pharmaceutical compositions comprising the step of mixing the active ingredients with a pharmacologically acceptable excipient.

A further object of the invention is the use of the compounds of the invention for the preparation of a medicament for the treatment of infections by multi-resistant Gram-positive strains.

Advantages offered by the present invention reside in obtaining new antibiotic compounds with activity equivalent to or comparable to that of linezolid against linezolid-susceptible bacterial strains but with greater effectiveness than linezolid against bacterial strains resistant to linezolid and/or to other antibiotics. In addition some of these substances possess cytotoxicity levels comparable to or less than that of linezolid.

DETAILED DESCRIPTION OF THE INVENTION

Figure 1:
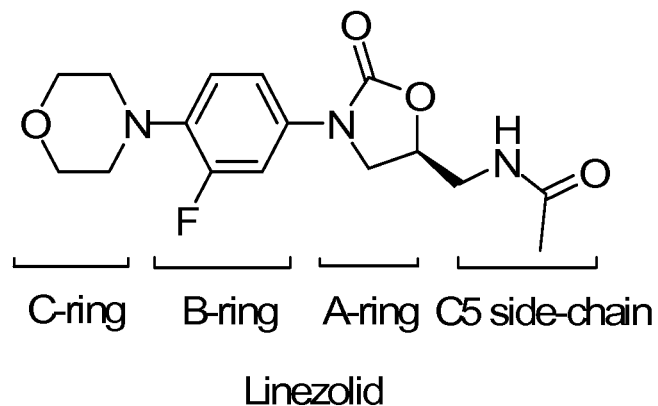
FIG. 1. Formula of linezolid with structural elements that compose it and nomenclature.

Compounds:

The chemical structure of the compounds of the present invention [formulas (I) and (II)] consists of an oxazolidinone ring (ring A), a phenyl ring (ring B), a five-membered heteroaromatic ring containing atoms Y, X and Z (ring C) and a side-chain linked to the C5 position of the oxazolidinone (C5-linked side-chain).

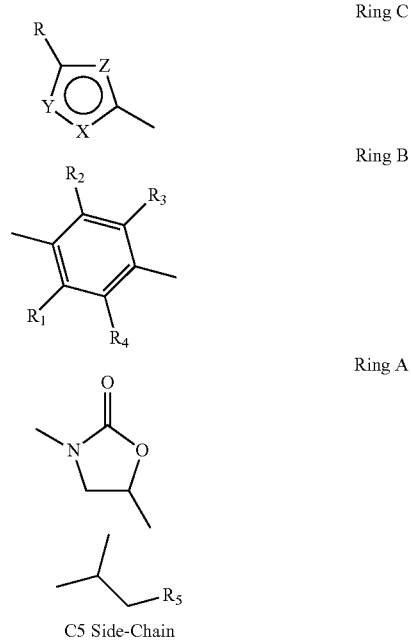

Ring C

Ring B

Ring A

C5 Side-Chain

Ring C

The ring C is an heterocycle where Y, X, and Z are, independently from each other, N, O, S atoms, or a —CH— group under the condition that t the ring contains at least two heteroatoms. Preferred formulas are those in which X is either O or S, or those in which Y is either N or —CH, and those in which Z is either N or —CH—. Majorly preferred formulas are those in which X is O and Y is N, or those in which X is O and Z is N. Even more preferred formulas are those in which X is O, Y is N, and Z is also N.

The R substituent on the ring C can be an hydrogen atom H (R=H) or a substituent chosen among: F, Cl, Br, I, methyl, ethyl, n-propyl, isopropyl, n-butyl, sec-butyl, ter-butyl, cyclopropyl, cyclobutyl, cyclopentyl, cyclohexyl, heteroaryl, —NH$_2$, NHCH$_3$, NHC$_2$H$_5$, —N(CH$_3$)$_2$, N(CH$_3$)(C$_2$H$_5$), —NC(=O)CH$_3$, —NC(=O)C$_2$H$_5$, —NH(cyclopropyl), NH(cyclobutyl), NH(cyclopentyl), NH(cyclohexyl), —OH, —OCH$_3$, —OC$_2$H$_5$, -On-Propyl, Oi-Propyl, —SH, SCH$_3$.

Ring B

Groups R$_1$, R$_2$, R$_3$, R$_4$ are, independently from each other, H, F, Cl, Br, CH$_3$, OH, OCH$_3$. At leas one of them is an halogen atom, for example R$_1$ is F, Cl, or Br, or R$_1$ and R$_2$ are F, Cl, or Br, or R$_1$, R$_2$, and R$_3$ are F or Cl. In a specific embodiment the halogen atom is F and the remaining R groups are hydrogen atoms. In a preferred formula, either R$_1$ or R$_4$ are F and the remaining "R"s are H.

C5 Side-Chain

The R$_5$ substituent in the C5 side-chain linked at the position 5 of the oxazolidinone nucleus is chosen within a group comprising the following radicals: I, —N$_3$, —NHC(=O)CH$_3$, —NHC(=S)CH$_3$, —NHC(=O)CH$_2$F, —NHC(=S)CH$_2$F, —NHC(=O)CH$_2$Cl, —NHC(=S)CH$_2$Cl, —NHC(=O)CH$_2$Br, —NHC(=S)CH$_2$Br, —NHC(=O)CHF$_2$, —NHC(=S)CHF$_2$, —NHC(=O)CHCl$_2$, —NHC(=S)CHCl$_2$, —NHC(=O)CHBr$_2$, —NHC(=S)CHBr$_2$, —NHC(=O)CF$_3$, —NHC(=S)CF$_3$, —NHC(=O)CCl$_3$, —NHC(=S)CCl$_3$, —NHC(=O)CBr$_3$, —NHC(=S)CBr$_3$, —NHC(=S)NH$_2$, —NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, —NHC(=O)NH-nC$_3$H$_7$, —NHC(=S)NH-nC$_3$H$_7$, —NHC(=O)NH-iC$_3$H$_7$, —NHC(=S)NH-iC$_3$H$_7$, NHC(=S)NH-cyclopropyl, —NHC(=O)NH-cyclopropyl, NHC(=S)NH-cyclobutyl, —NHC(=O)NH-cyclobutyl, NHC(=S)NH-cyclopentyl, —NHC(=O)NH-cyclopentyl, NHC(=S)NH-cyclohexyl, —NHC(=O)NH-cyclohexyl, NHC(=O)NHC(=O)CH$_3$, NHC(=S)NHC(=O)CH$_3$ NHC(=O)NHC(=O)C$_2$H$_5$, NHC(=O)NH-heteroaryl, —NCS, pyrrolyl, pyrazolyl, imidazolyl, 1,2,3-triazol-1-yl, 1,2,4-triazol-1-yl.

Considering the asymmetric configuration of the carbon atom in position 5 of the ring A, all above identified compounds are optically active. Therefore, the present invention concerns: racemic mixtures of these compounds, mixtures enriched in either one of the enantiomers, and either one of the isolated enantiomers. For the scopes of the present invention it is understood as racemic mixture a 50%:50% mixture of the two R and S enantiomers. It is understood as mixture enriched in one of the enantiomers a mixture containing more than 50% of one enantiomer (either S or R), for example 55%, 60%, 65%, 70%, 75%, or more. As isolated enantiomer it is understood a pure enantiomer, i.e. 100% or a mixture highly enriched of that enantiomer, for example 98%, 95%, 93%, 90%, 88%, 85%, 80%.

A specific form of embodiment of the invention implies compounds consisting of the S enantiomer or compositions comprising the S enantiomer as either enriched mixture or pure enantiomer. A second specific form of embodiment of the invention comprises compounds consisting of the R/S racemic mixtures or compositions comprising the R/S racemic mixtures. A further form of specific embodiment, implies mixture enriched in the R enantiomer.

Preferred compounds having general formula (II) are listed in Table 1 below.

TABLE 1

|  | R | R1 | R2 | R3 | R4 | R5 |
|---|---|---|---|---|---|---|
| 1 | H | H | H | H | H | NHC(=O)CH$_3$ |
| 2 | H | F | H | H | H | NHC(=O)CH$_3$ |
| 3 | H | F | F | H | H | NHC(=O)CH$_3$ |
| 4 | H | F | F | F | H | NHC(=O)CH$_3$ |
| 5 | H | F | F | F | H | NHC(=O)CH$_3$ |
| 6 | H | Cl | H | H | H | NHC(=O)CH$_3$ |
| 7 | H | Cl | Cl | H | H | NHC(=O)CH$_3$ |
| 8 | H | H | H | H | H | NHC(=S)CH$_3$ |
| 9 | H | F | H | H | H | NHC(=S)CH$_3$ |
| 10 | H | F | F | H | H | NHC(=S)CH$_3$ |
| 11 | H | Cl | H | H | H | NHC(=S)CH$_3$ |
| 12 | H | Cl | Cl | H | H | NHC(=S)CH$_3$ |
| 13 | H | F | F | F | H | NHC(=S)CH$_3$ |
| 14 | H | Br | H | H | H | NHC(=S)CH$_3$ |
| 15 (A3a) | CH$_3$ | H | H | H | H | NHC(=O)CH$_3$ |

TABLE 1-continued

| | R | R1 | R2 | R3 | R4 | R5 |
|---|---|---|---|---|---|---|
| 16 (A3b) | CH$_3$ | F | H | H | H | NHC(=O)CH$_3$ |
| 17 | CH$_3$ | F | F | H | H | NHC(=O)CH$_3$ |
| 18 | CH$_3$ | F | F | F | H | NHC(=O)CH$_3$ |
| 19 | CH$_3$ | Cl | H | H | H | NHC(=O)CH$_3$ |
| 20 | CH$_3$ | Cl | Cl | H | H | NHC(=O)CH$_3$ |
| 21 | CH$_3$ | Br | H | H | H | NHC(=O)CH$_3$ |
| 22 (A4a) | CH$_3$ | H | H | H | H | NHC(=S)CH$_3$ |
| 23 (A4b) | CH$_3$ | F | H | H | H | NHC(=S)CH$_3$ |
| 24 | CH$_3$ | F | F | H | H | NHC(=S)CH$_3$ |
| 25 | CH$_3$ | Cl | H | H | H | NHC(=S)CH$_3$ |
| 26 | CH$_3$ | Cl | Cl | H | H | NHC(=S)CH$_3$ |
| 27 | CH$_3$ | F | F | F | H | NHC(=S)CH$_3$ |
| 28 | CH$_3$ | Br | H | H | H | NHC(=S)CH$_3$ |
| 29 | C$_2$H$_5$ | H | H | H | H | NHC(=O)CH$_3$ |
| 30 | C$_2$H$_5$ | F | H | H | H | NHC(=O)CH$_3$ |
| 31 | C$_2$H$_5$ | F | F | H | H | NHC(=O)CH$_3$ |
| 32 | C$_2$H$_5$ | F | F | F | H | NHC(=O)CH$_3$ |
| 33 | C$_2$H$_5$ | Cl | H | H | H | NHC(=O)CH$_3$ |
| 34 | C$_2$H$_5$ | Cl | Cl | H | H | NHC(=O)CH$_3$ |
| 35 | C$_2$H$_5$ | Br | H | H | H | NHC(=O)CH$_3$ |
| 36 | C$_2$H$_5$ | H | H | H | H | NHC(=S)CH$_3$ |
| 37 | C$_2$H$_5$ | F | H | H | H | NHC(=S)CH$_3$ |
| 38 | C$_2$H$_5$ | F | F | H | H | NHC(=S)CH$_3$ |
| 39 | C$_2$H$_5$ | Cl | H | H | H | NHC(=S)CH$_3$ |
| 40 | C$_2$H$_5$ | Cl | Cl | H | H | NHC(=S)CH$_3$ |
| 41 | C$_2$H$_5$ | F | F | F | H | NHC(=S)CH$_3$ |
| 42 | C$_2$H$_5$ | Br | H | H | H | NHC(=S)CH$_3$ |
| 43 | H | H | H | H | H | NHC(=O)NH$_2$ |
| 44 | H | F | H | H | H | NHC(=O)NH$_2$ |
| 45 | H | F | F | H | H | NHC(=O)NH$_2$ |
| 46 | H | F | F | F | H | NHC(=O)NH$_2$ |
| 47 | H | Br | H | H | H | NHC(=O)NH$_2$ |
| 48 | H | Cl | H | H | H | NHC(=O)NH$_2$ |
| 49 | H | Cl | Cl | H | H | NHC(=O)NH$_2$ |
| 50 | H | H | H | H | H | NHC(=S)NH$_2$ |
| 51 | H | F | H | H | H | NHC(=S)NH$_2$ |
| 52 | H | F | F | H | H | NHC(=S)NH$_2$ |
| 53 | H | Cl | H | H | H | NHC(=S)NH$_2$ |
| 54 | H | Cl | Cl | H | H | NHC(=S)NH$_2$ |
| 55 | H | F | F | F | H | NHC(=S)NH$_2$ |
| 56 | H | Br | H | H | H | NHC(=S)NH$_2$ |
| 57 | CH$_3$ | H | H | H | H | NHC(=O)NH$_2$ |
| 58 | CH$_3$ | F | H | H | H | NHC(=O)NH$_2$ |
| 59 | CH$_3$ | F | F | H | H | NHC(=O)NH$_2$ |
| 60 | CH$_3$ | F | F | F | H | NHC(=O)NH$_2$ |
| 61 | CH$_3$ | Cl | H | H | H | NHC(=O)NH$_2$ |
| 62 | CH$_3$ | Cl | Cl | H | H | NHC(=O)NH$_2$ |
| 63 | CH$_3$ | Br | H | H | H | NHC(=O)NH$_2$ |
| 64 B3a | CH$_3$ | H | H | H | H | NHC(=S)NH$_2$ |
| 65 B3b | CH$_3$ | F | H | H | H | NHC(=S)NH$_2$ |
| 66 | CH$_3$ | F | F | H | H | NHC(=S)NH$_2$ |
| 67 | CH$_3$ | Cl | H | H | H | NHC(=S)NH$_2$ |
| 68 | CH$_3$ | Cl | Cl | H | H | NHC(=S)NH$_2$ |
| 69 | CH$_3$ | F | F | F | H | NHC(=S)NH$_2$ |
| 70 | CH$_3$ | Br | H | H | H | NHC(=S)NH$_2$ |
| 71 | C$_2$H$_5$ | H | H | H | H | NHC(=O)NH$_2$ |
| 72 | C$_2$H$_5$ | F | F | H | H | NHC(=O)NH$_2$ |
| 73 | C$_2$H$_5$ | F | F | H | H | NHC(=O)NH$_2$ |
| 74 | C$_2$H$_5$ | F | F | F | H | NHC(=O)NH$_2$ |
| 75 | C$_2$H$_5$ | Cl | H | H | H | NHC(=O)NH$_2$ |
| 76 | C$_2$H$_5$ | Cl | Cl | H | H | NHC(=O)NH$_2$ |
| 77 | C$_2$H$_5$ | Br | H | H | H | NHC(=O)NH$_2$ |
| 78 | C$_2$H$_5$ | H | H | H | H | NHC(=S)NH$_2$ |
| 79 | C$_2$H$_5$ | F | H | H | H | NHC(=S)NH$_2$ |
| 80 | C$_2$H$_5$ | F | F | H | H | NHC(=S)NH$_2$ |
| 81 | C$_2$H$_5$ | Cl | H | H | H | NHC(=S)NH$_2$ |
| 82 | C$_2$H$_5$ | Cl | Cl | H | H | NHC(=S)NH$_2$ |
| 83 | C$_2$H$_5$ | F | F | F | H | NHC(=S)NH$_2$ |
| 84 | C$_2$H$_5$ | Br | H | H | H | NHC(=S)NH$_2$ |
| 85 | H | H | H | H | H | NHC(=O)NHCH$_3$ |
| 86 | H | F | H | H | H | NHC(=O)NHCH$_3$ |
| 87 | H | F | F | H | H | NHC(=O)NHCH$_3$ |
| 88 | H | F | F | F | H | NHC(=O)NHCH$_3$ |
| 89 | H | Br | H | H | H | NHC(=O)NHCH$_3$ |
| 90 | H | Cl | H | H | H | NHC(=O)NHCH$_3$ |
| 91 | H | Cl | Cl | H | H | NHC(=O)NHCH$_3$ |
| 92 | H | H | H | H | H | NHC(=S)NHCH$_3$ |
| 93 | H | F | H | H | H | NHC(=S)NHCH$_3$ |
| 94 | H | F | F | H | H | NHC(=S)NHCH$_3$ |
| 95 | H | Cl | H | H | H | NHC(=S)NHCH$_3$ |
| 96 | H | Cl | Cl | H | H | NHC(=S)NHCH$_3$ |
| 97 | H | F | F | F | H | NHC(=S)NHCH$_3$ |
| 98 | H | Br | H | H | H | NHC(=S)NHCH$_3$ |
| 99 | CH$_3$ | H | H | H | H | NHC(=O)NHCH$_3$ |
| 100 | CH$_3$ | F | H | H | H | NHC(=O)NHCH$_3$ |
| 101 | CH$_3$ | F | F | H | H | NHC(=O)NHCH$_3$ |
| 102 | CH$_3$ | F | F | F | H | NHC(=O)NHCH$_3$ |
| 103 | CH$_3$ | Cl | H | H | H | NHC(=O)NHCH$_3$ |
| 104 | CH$_3$ | Cl | Cl | H | H | NHC(=O)NHCH$_3$ |
| 105 | CH$_3$ | Br | H | H | H | NHC(=O)NHCH$_3$ |
| 106 B4a | CH$_3$ | H | H | H | H | NHC(=S)NHCH$_3$ |
| 107 B4b | CH$_3$ | F | H | H | H | NHC(=S)NHCH$_3$ |
| 108 | CH$_3$ | F | F | H | H | NHC(=S)NHCH$_3$ |
| 109 | CH$_3$ | Cl | H | H | H | NHC(=S)NHCH$_3$ |
| 110 | CH$_3$ | Cl | Cl | H | H | NHC(=S)NHCH$_3$ |
| 111 | CH$_3$ | F | F | F | H | NHC(=S)NHCH$_3$ |
| 112 | CH$_3$ | Br | H | H | H | NHC(=S)NHCH$_3$ |
| 113 | C$_2$H$_5$ | H | H | H | H | NHC(=O)NHCH$_3$ |
| 114 | C$_2$H$_5$ | F | H | H | H | NHC(=O)NHCH$_3$ |
| 115 | C$_2$H$_5$ | F | F | H | H | NHC(=O)NHCH$_3$ |
| 116 | C$_2$H$_5$ | F | F | F | H | NHC(=O)NHCH$_3$ |
| 117 | C$_2$H$_5$ | Cl | H | H | H | NHC(=O)NHCH$_3$ |
| 118 | C$_2$H$_5$ | Cl | Cl | H | H | NHC(=O)NHCH$_3$ |
| 119 | C$_2$H$_5$ | Br | H | H | H | NHC(=O)NHCH$_3$ |
| 120 | C$_2$H$_5$ | H | H | H | H | NHC(=S)NHCH$_3$ |
| 121 | C$_2$H$_5$ | F | H | H | H | NHC(=S)NHCH$_3$ |
| 122 | C$_2$H$_5$ | F | F | H | H | NHC(=S)NHCH$_3$ |
| 123 | C$_2$H$_5$ | Cl | H | H | H | NHC(=S)NHCH$_3$ |
| 124 | C$_2$H$_5$ | Cl | Cl | H | H | NHC(=S)NHCH$_3$ |
| 125 | C$_2$H$_5$ | F | F | F | H | NHC(=S)NHCH$_3$ |
| 126 | C$_2$H$_5$ | Br | H | H | H | NHC(=S)NHCH$_3$ |
| 127 B2a | CH$_3$ | H | H | H | H | NCS |
| 128 B2b | CH$_3$ | F | H | H | H | NCS |
| 129 | CH$_3$ | F | F | H | H | NCS |
| 130 | CH$_3$ | Cl | H | H | H | NCS |
| 131 | CH$_3$ | Cl | Cl | H | H | NCS |
| 132 | CH$_3$ | F | F | F | H | NCS |
| 133 | CH$_3$ | Br | H | H | H | NCS |
| 134 | CH$_3$ | H | H | H | H | NHC(=O)NHC(=O)CH$_3$ |
| 135 | CH$_3$ | F | H | H | H | NHC(=O)NHC(=O)CH$_3$ |
| 136 | CH$_3$ | F | F | H | H | NHC(=O)NHC(=O)CH$_3$ |
| 137 | CH$_3$ | Cl | H | H | H | NHC(=O)NHC(=O)CH$_3$ |
| 138 | CH$_3$ | Cl | Cl | H | H | NHC(=O)NHC(=O)CH$_3$ |
| 139 | CH$_3$ | F | F | F | H | NHC(=O)NHC(=O)CH$_3$ |
| 140 | CH$_3$ | Br | H | H | H | NHC(=O)NHC(=O)CH$_3$ |
| 141 | CH$_3$ | H | H | H | H | NHC(=S)NHC(=O)CH$_3$ |
| 142 | CH$_3$ | F | H | H | H | NHC(=S)NHC(=O)CH$_3$ |
| 143 | CH$_3$ | F | F | H | H | NHC(=S)NHC(=O)CH$_3$ |
| 144 | CH$_3$ | Cl | H | H | H | NHC(=S)NHC(=O)CH$_3$ |
| 145 | CH$_3$ | Cl | Cl | H | H | NHC(=S)NHC(=O)CH$_3$ |
| 146 | CH$_3$ | F | F | F | H | NHC(=S)NHC(=O)CH$_3$ |
| 147 | CH$_3$ | Br | H | H | H | NHC(=S)NHC(=O)CH$_3$ |
| 148 A1a | CH$_3$ | H | H | H | H | I |
| 149 A1b | CH$_3$ | F | H | H | H | I |

TABLE 1-continued

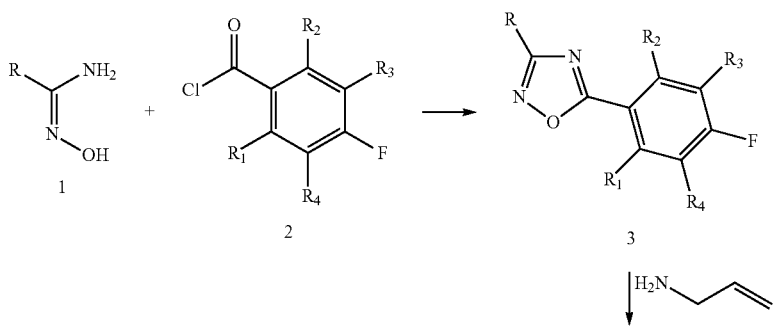

| | R | R1 | R2 | R3 | R4 | R5 |
|---|---|---|---|---|---|---|
| 150 | $CH_3$ | F | F | H | H | I |
| 151 | $CH_3$ | Cl | H | H | H | I |
| 152 | $CH_3$ | Cl | Cl | H | H | I |
| 153 | $CH_3$ | F | F | F | H | I |
| 154 | $CH_3$ | Br | H | H | H | I |
| 155 B1a | $CH_3$ | H | H | H | H | 1,2,3-triazol-1-yl |
| 156 B1b | $CH_3$ | F | H | H | H | 1,2,3-triazol-1-yl |
| 157 | $CH_3$ | F | F | H | H | 1,2,3-triazol-1-yl |
| 158 | $CH_3$ | Cl | H | H | H | 1,2,3-triazol-1-yl |
| 159 | $CH_3$ | Cl | Cl | H | H | 1,2,3-triazol-1-yl |
| 160 | $CH_3$ | F | F | F | H | 1,2,3-triazol-1-yl |
| 161 | $CH_3$ | Br | H | H | H | 1,2,3-triazol-1-yl |

Each compound identified above is intended as the S enantiomer as well as a mixture enriched with the S enantiomer or a racemic mixture, with the exception of those in which R5 is —I, —NCS, 1,2,3 triazol-1-yl, where they are intended as pure R enantiomer or a mixture enriched with the R enantiomer or a racemic mixture.

Preparation of Invented Compounds

The synthesis of compounds of interest A and B and of the corresponding intermediates, is described below. The invented compounds were synthesized starting from the construction of the 1,2,4-oxadiazole ring by following the classic amidoxime route (Scheme 1) as reported in [9]. Thus, amidoxime 1 was reacted with the corresponding benzoyl chloride 2, producing 1,2,4-oxadiazoles 3. The latter compounds, where the para position is activated to undergo an Aromatic Nucleophilic Substitution, [10-13] were with allylamine, yielding compounds 4. Reaction with di-(t-butyl)-dicarbonate and subsequent cyclization [14] of the resulting derivatives 5, yielded oxazolidinones of interest A1 as ideal precursors for further side-chain modifications.

Scheme 1

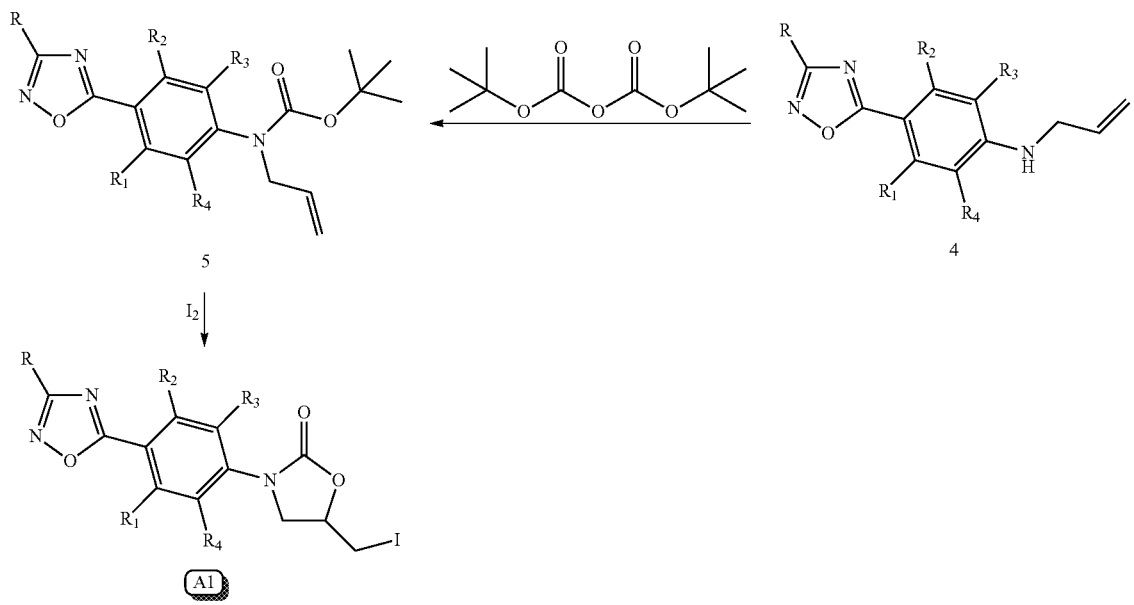

The subsequent functionalization of the side-chain (Scheme 2) included the acetamidomethyl moiety A3, as well as the corresponding thioamides A4, thioureas B4 and azolic derivatives A5-7, B1.

The azide precursors A2 were obtained by reaction of compounds A1 with an azide source. Their subsequent reduction yielded the corresponding amino derivatives 6 [15]. The amino derivatives 6 were readily reacted with acetyl chloride or acetic anhydride, giving compounds A3. The acetamidomethyl derivatives A3, were reacted with sulfurating reagents (i.e. Lawesson's Reagent or $P_{2S5}$) yielding thioamide derivatives A4 (Scheme 2).

The azole derivatives A5-7, B1, were obtained by means of nucleophilic substitution starting from iodo-derivatives A1, while (thio)ureas B4 were obtained through reactions of amines 6 with iso(thio)cyanates (Scheme 2).

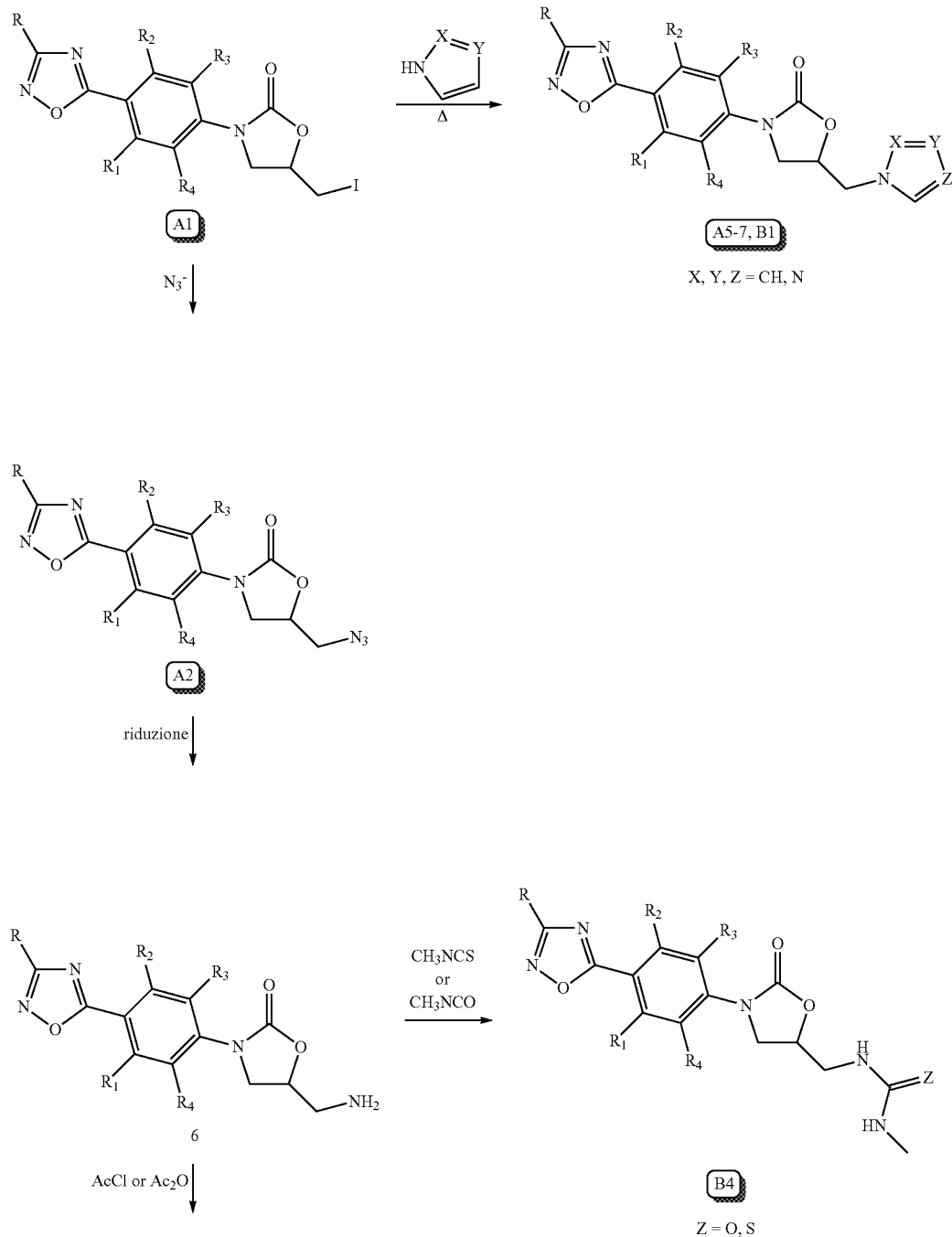

Scheme 2

-continued

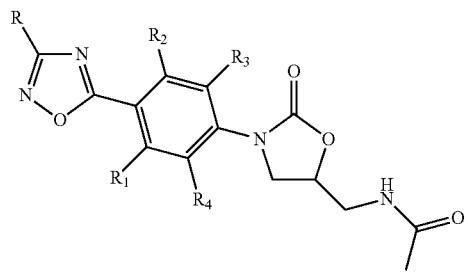

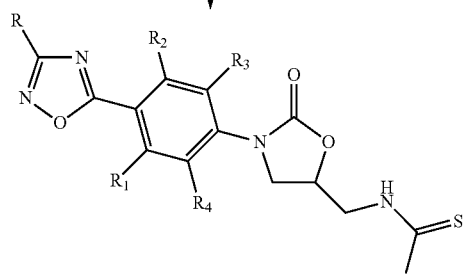

The so obtained compounds, synthesized as racemic mixtures, were resolved into the corresponding enantiomers (S or R) through HPLC separations by using a chiral stationary phase.

The Pharmaceutical Compositions

Pharmaceutical compositions suitable for administration of the compounds of the invention are compositions designed for oral, parenteral or topical usage.

Oral compositions may be for example in the form of tablet, coated tablet, hard capsule, soft capsule, syrup, solution, suspension, emulsion. Parenteral compositions may be for example in the form of aqueous or oily solution or emulsion. Topical compositions may be for example in the form of ointment, cream, gel, solution, emulsion O/W or W/O, or suspension.

In the preparation of pharmaceutical compositions one or more compounds of the invention are mixed with various therapeutically acceptable excipients suitable for solid, liquid or pasty compositions.

Therapeutic Applications

The claimed compounds are new antibiotics intended for use in the treatment of infections caused by bacteria, essentially by Gram-positive extremely resistant bacteria. For example, but not limited to, *Staphylococcus* spp, *Enterococcus* spp, *Streptococcus* spp, in particular in the treatment of infections caused by *Staphylococcus aureus, Staphylococcus epidermidis, Enterococcus faecium, Enterococcus faecalis, Streptococcus pneumoniae, Haemophilus influenzae, Haemophilus parainfluenzae, Moraxella catarrhalis*. The compounds of the invention have proved to be active also on bacteria resistant to other antibiotics or resistant to the reference compound linezolid. Advantageously, the compounds of the invention are effective even against bacteria resistant to more than one antibiotic, against multi-resistant bacteria, for example to two or more antibiotics selected from methicillin, vancomycin, penicillin, macrolides, fluoroquinolones or linezolid. Furthermore, the novel compounds of the invention combine the inhibitory activity or bactericidal against bacteria both susceptible or (multi) resistant to known antibiotics to a entirely acceptable toxicity or even less than that of the reference compound linezolid, thus offering an entirely beneficial clinical/therapeutic profile.

EXPERIMENTAL SECTION

Evaluation of the Pharmacological Activity
Microbiological Assays
(i) Bacterial Strains Several well characterized for their antibiotic-susceptibility phenotype *Staphylococcus aureus* isolates were used for the determination of the in vitro antibacterial activity of the studied compounds. In particular, *S. aureus* ATCC 29213 reference standard strain and *S. aureus* M923 (collection strain) were used as MSSA strains. Among MRSA, *S. aureus* MU50 (ATCC 700699) reference standard strain and two collection strains (433 and F511) were used for susceptibility assays.

(ii) Determination of Minimum Inhibitory Concentrations (MICs)

The in vitro antibacterial activity of the new agents was studied by determining their minimum inhibitory concentrations (MICs) by means of the broth microdilution method according to the Clinical and Laboratory Standards Institute (CLSI) guidelines. [16] Briefly, serial 2-fold dilutions of each compound were made using the Cation adjusted Mueller-Hinton broth (CAMHB) in microtitre plates with 96 wells. Dimethyl sulfoxide (DMSO) was used as solvent for all the synthetized compounds. An equal volume of the bacterial inoculum ($1\times10^6$ CFU/mL) was added to each well on the microtitre plate containing 0.05 mL of the serial antibiotic dilutions. The microtitre plate was then incubated at 37° C. for 18-24 h after which each well was analysed for the presence of bacterial growth. The MIC was defined as the lowest concentration of antimicrobial agent able to cause inhibition of bacterial growth as shown by the lack of turbidity of the culture medium. The in vitro antibacterial activities of new linezolid-like 1,2,4-oxadiazoles were tested and compared to that of reference oxazolidinone in clinical use: Linezolid (Zyvox®, Pfizer). Final DMSO concentrations were also taken into account in all the biological assays.

Minimum Inhibitory Concentration Test

Fourteen new compounds in racemic mixture (group A), as following shown, were analyzed for their antibacterial activity against strains of *Staphylococcus aureus* in terms of reference standard strains and clinical strains, both methicillin-susceptible (MSSA) or methicillin-resistant (MRSA).

A1-7a,b

| | $R_1$ | $R_2$ |
|---|---|---|
| A1a | H | I |
| A1b | F | I |
| A2a | H | $N_3$ |
| A2b | F | $N_3$ |
| A3a | H | NH(C=O)CH$_3$ |
| A3b | F | NH(C=O)CH$_3$ |
| A4a | H | NH(C=S)CH$_3$ |
| A4b | F | NH(C=S)CH$_3$ |
| A5a | H | pirazol-1-il |
| A5b | F | pirazol-1-il |
| A6a | H | imidazol-1-il |
| A6b | F | imidazol-1-il |
| A7a | H | 1,2,4-triazol-1-il |
| A7b | F | 1,2,4-triazol-1-il |

The antimicrobial activities, summarized in Table 2, were determined by the "gold standard" method of broth microdilution, as recommended by the Clinical Laboratory Standards Institute (CLSI) (See the Experimental Section). The minimum inhibitory concentrations (MIC) values were expressed in μg/mL, and cell viability tests were performed to evaluate the antibacterial selective toxicity of most active compounds. Linezolid has been used as a reference antibiotic. In detail, the bacterial strains were tested: *Staphylococcus aureus* ATCC 29213, a clinical strain of methicillin-susceptible *S. aureus* (M923), *S. aureus* MU50 (methicillin-resistant—MRSA), and two methicillin-resistant clinical strains, 433 and F511. All strains tested were found to be linezolid-susceptible. Among these molecules the most active, in racemic form, have proved to be A4a and A4b compounds.

TABLE 2

| | MIC (μg/mL) | | | | |
|---|---|---|---|---|---|
| Comp. A | ATCC 29213 | MSSA M923 | MRSA MU50 | MRSA 433 | MRSA F511 |
| A1a | >50 | >50 | 50 | 25 | 50 |
| A1b | >50 | >50 | 50 | 50 | >50 |

TABLE 2-continued

| | MIC (μg/mL) | | | | |
|---|---|---|---|---|---|
| Comp. A | ATCC 29213 | MSSA M923 | MRSA MU50 | MRSA 433 | MRSA F511 |
| A2a | >50 | >50 | >50 | >50 | >50 |
| A2b | >50 | >50 | >50 | >50 | >50 |
| A3a | 12.5 | 6.25 | 6.25 | 1.6 | 12.5 |
| A3b | 12.5 | 6.25 | 6.25 | 1.6 | 12.5 |
| A4a | 3.13 | 1.6 | ≤0.4 | 1.6 | 1.6 |
| A4b | 1.6 | 1.6 | ≤0.4 | 0.8 | 1.6 |
| A5a | >50 | >50 | >50 | >50 | >50 |
| A5b | >50 | >50 | >50 | >50 | >50 |
| A6a | >50 | >50 | >50 | >50 | >50 |
| A6b | >50 | >50 | >50 | >50 | >50 |
| A7a | >50 | >50 | >50 | >50 | >50 |
| A7b | >50 | >50 | >50 | >50 | >50 |
| Linezolid | ≤0.4 | 3.13 | 0.8 | 1.6 | 3.13 |

Compounds A3a, A3b, A4a, A4b, A1a, A1b correspond to the compounds 15, 16, 22, 23, 148 and 149 of Table 1

Four of the fourteen tested compounds (see Table 2) showed MIC values, both against MSSA and MRSA strains with potency comparable or superior to that of linezolid. Furthermore, a better activity against MSSA and MRSA strains compared to linezolid has been displayed by derivatives containing sulfur A4a and A4b, while compounds A3a, and A3b were shown to be less active than linezolid, except for the MRSA strain 433. The comparison with the linezolid should take account of the fact that the tested compounds were used as a racemic mixture, then the antibacterial activity of A3a, A3b, A4a and A4b is presumed to be underestimated compared to the pure more active enantiomer.

Of other compounds (group B), shown below, were assessed the activities of both the racemic mixture and S and R enantiomers.

B1-4a,b

| | $R_1$ | $R_2$ |
|---|---|---|
| B1a | H | 1,2,3-triazol-1-il |
| B1b | F | 1,2,3-triazol-1-il |
| B2a | H | NCS |
| B2b | F | NCS |
| B3a | H | NH(C=S)NH$_2$ |
| B3b | F | NH(C=S)NH$_2$ |
| B4a | H | NH(C=S)NHCH$_3$ |
| B4b | F | NH(C=S)NHCH$_3$ |

The antimicrobial activities, summarized in Table 3, were determined by the "gold standard" method of broth microdilution, as recommended by the Clinical Laboratory Standards Institute (CLSI) (See the Experimental Section). The minimum inhibitory concentration (MIC) values were expressed in μg/mL. Linezolid has been used as a reference antibiotic. In detail, the tested bacterial strains were: *Staphylococcus aureus* ATCC 29213, a clinical strain of methicillin-susceptible *S. aureus* (M923), *S. aureus* MU50 (methicillin-resistant—MRSA) strain, and two methicillin-resistant clinical strains, 433 and F511. All strains tested were found to be linezolid-susceptible. Among tested new molecules the most active, in racemic form, have proved to be B4a and B4b compounds, followed by B1a and B1b possessing a fair amount of activity (Table 3).

TABLE 3

| Comp. B | MIC (μg/mL) | | | | |
|---|---|---|---|---|---|
| | ATCC 29213 | MSSA M923 | MRSA MU50 | MRSA 433 | MRSA F511 |
| B1a | 25 | 25 | 3.125 | 12.5 | 12.5 |
| B1b | 25 | 25 | 1.6 | 6.25 | 12.5 |
| B2a | >50 | >50 | >50 | >50 | 50 |
| B2b | >50 | >50 | >50 | >50 | >50 |
| B3a | >50 | >50 | >50 | >50 | >50 |
| B3b | >50 | >50 | >50 | >50 | >50 |
| B4a | 6.25 | 6.25 | 1.6 | 3.125 | 6.25 |
| B4b | 6.25 | 6.25 | 1.6 | 3.125 | 6.25 |
| Linezolid | ≤0.4 | 3.125 | 0.8 | 1.6 | 3.125 |

Among these, B4a and B4b compounds (corresponding to compounds 106 and 107 of Table 1) showed an antibacterial activity very similar to that of linezolid against linezolid-susceptible *S. aureus* strains.

In a completely surprising manner, the same compounds, resolved into their enantiomers, have demonstrated efficacy from 4 to 8 times higher than linezolid against linezolid-resistant *Staphylococcus* spp. strains. The results are reported in Table 4. In one case it is completely reversed resistance to linezolid into susceptibility. Of these molecules enantiomeric separations have allowed to assign the power to the S enantiomer, while the R proved to be inactive (see Table 4). The compounds B4a and B4b correspond to racemic mixtures of the two compounds B4a and B4b, the compounds B4bS and B4bR and B4aS and B4aR are resolved S and R enantiomers, respectively.

TABLE 4

| | Valori MIC MIC-range ≤0.06 a >128 μg/ml | | | | | | | |
|---|---|---|---|---|---|---|---|---|
| Composti | B4b | B4bS | B4bR | B4a | B4aS | B4aR | LZD | DA |
| Ceppi saggiati: 6 ATCC (4MSSA e 2 MRSA) piu 45 MRSA tutti LZD sensibili | | | | | | | | |
| MIC-range | 0.5-16 | 0.5-8 | 64->128 | 1-16 | 0.5-8 | 128->128 | 0.25-16 | <0.06->128 |
| MIC$_{50}$ | 4 | 2 | >128 | 8 | 2 | >128 | 2 | <0.06 |
| MIC$_{90}$ | 16 | 4 | >128 | 16 | 4 | >128 | 4 | >128 |
| Ceppi saggiati: 12 MRSE tutti LZD resistenti | | | | | | | | |
| MIC range | 32->128 | 8.16 | >128 | 32->128 | 8-32 | >128 | 32-64 | 0.12-1 |
| MIC$_{50}$ | 64 | 8 | >128 | 64 | 16 | >128 | 32 | 0.5 |
| MIC$_{90}$ | 128 | 8 | >128 | >128 | 32 | >128 | 64 | 1 |

Cell Viability (Citotoxicity Assay)

To assess if the effect shown against bacterial cells could be related to a selected toxicity or to a more general toxic effect, we performed a first level assay in different types of eukaryotic cell lines to screen the new compounds for their general cytotoxic activity.

Cell Viability

The effects of A4b, (compound 23 of Table 1) and linezolid on cells viability were in vitro studied on PK15 (porcine kidney epithelial), HaCaT (human keratinocytes), and HepG2 (human hepatocellular carcinoma) cell lines. [17-19] HepG2 and HaCat cells were grown in Dulbecco's modified eagles medium (DMEM) whereas PK15 in DMEM/M199 (1:1). All media were supplemented with 10% heat inactivated foetal bovine serum (FBS), 2 mM L-glutamine, 100 units/mL penicillin and 100 μg/mL streptomycin. Cells were maintained at 37° C. in a 5% $CO_2$ atmosphere. All reagents for cell culture were from Euroclone (Pero, Italy).

Cell viability was measured by the MTT assay.[20] Briefly, MTT [3-(4,5-Dimethylhiazol-2-yl)-2,5-diphenyltetrazolium bromide] stock solution (5 mg/mL) was added to each well to a final concentration of 1.2 mM, and cells were incubated for 1 hour and 30 minutes at 37° C. After removing MTT solution, the reaction was stopped by adding 90% ethanol. Resuspended cells were centrifuged 10 min at 800×g. The absorbance was measured with the multilabel Victor$^3$ spectrophotometer (Perkin Elmer, Turku, Finland) at wavelength of 570 nm. Data are means±S.E. of 3 separate experiments performed in triplicate.

Statistical Analysis

Statistical significance was obtained with Student's test in comparison with controls *=P<0.05, =P<0.001. Data are means±S.E. of 3 separate experiments performed in triplicate.

All tested cell lines were treated with increasing concentrations (5-400 μg/mL) of A4a, and linezolid as reference compound. Another control was DMSO used as solvent.

Figure 2:
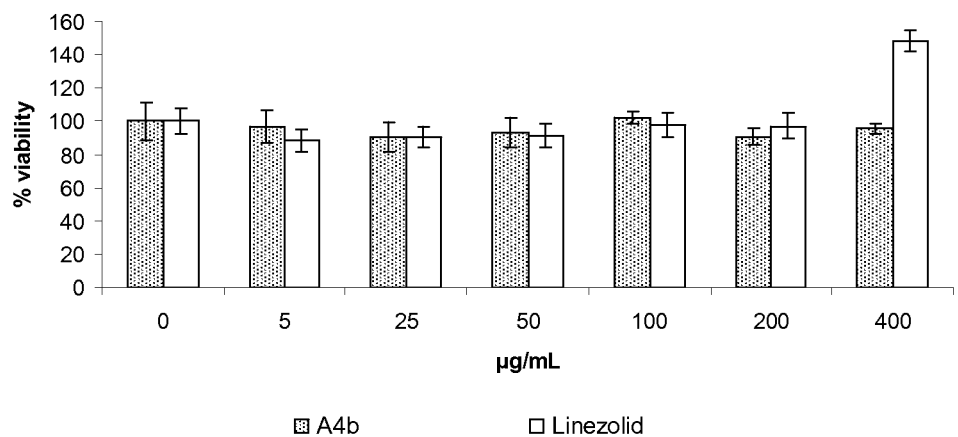
FIG. 2. Results of cell viability assays on PK15 cells treated with the A4b compound (compound 23 of table 1) and linezolid. Limits of significance: *=P<0.05, **=P<0.01.

The A4b molecule induced a moderate reduction of viability (less than 10%) in the PK15 cell line, with statistical significance at the concentrations of 25 (P<0.01), 50 (P<0.05) and 200 μg/mL (P<0.05), respectively (FIG. 2). This trend is comparable to that obtained with linezolid at the same concentrations.

Figure 3:
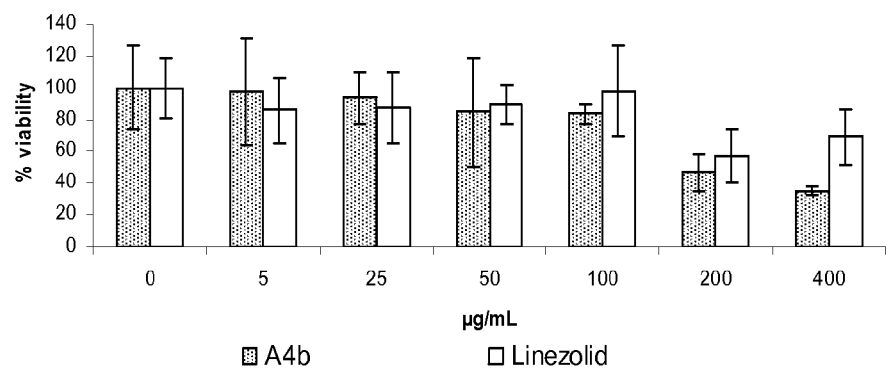
FIG. 3. Results of cell viability assays on HaCaT cells treated with the A4b compound (compound 23 of table 1) and linezolid. Limits of significance: *=P<0.05, **=P<0.01.

The reduction of cell viability caused by the A4b molecule was slightly more evident in the HaCaT cell line, reaching levels of statistically significant mortality compared to the values obtained with linezolid only at a concentration of 400 μg/mL (P<0.01; FIG. 3).

Figure 4:
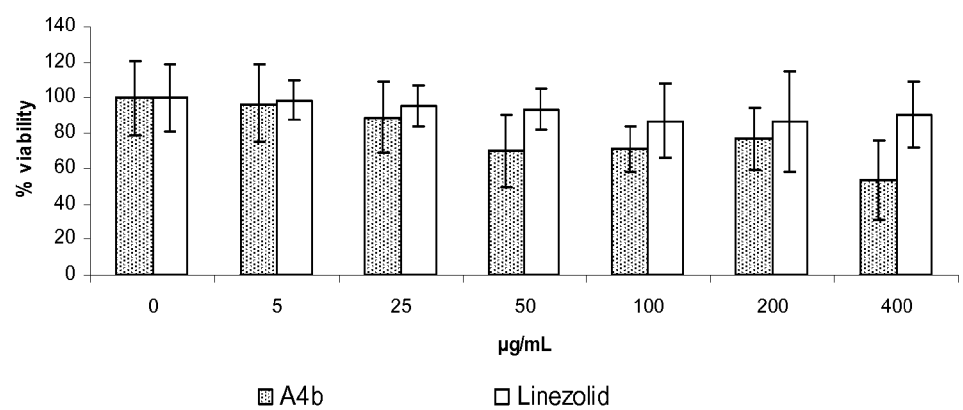
FIG. 4. Results of cell viability on HepG2 cells treated with the A4b compound (compound 23 of table 1) and linezolid. Limits of significance: *=P<0.05, **=P<0.01.

HepG2 cells showed a reduction in viability from 50 μg/mL of the A4b compound (FIG. 4).

They were then in vitro evaluated the effects of B4a and B4b molecules on cell viability on human hepatoma cell line, HepG2 and comparison with cytotoxicity induced by linezolid (negative control).

The cells are cultured in Dulbecco's modified eagles medium (DMEM) supplemented by 10% heat inactivated fetal bovine serum (FBS), L-glutamine at a final concentration of 2 mM, 100 units/mL of penicillin and 100 micrograms/mL of streptomycin. The cells were maintained at 37° C. in a 5% of $CO_2$ atmosphere. Cytotoxic treatment: cells, plated at a density of 40,000 cell/cm² and maintained in culture for two days, were treated for 48 hours with increasing concentrations (25-100 μg/ml) of both enantiomers of B4a and B4b substances.

Cell viability was evaluated by an PrestoBlue® Cell Viability Reagent assay, a solution containing resazurin that permeates into cells and exploits the reducing power when they are alive and metabolically active. Briefly, the PrestoBlue® solution is administered directly to the medium of the cells in culture following the instructions of the manufacturer that has supplied the product. The cells are incubated for 1 hour at 37° C., at which time the PrestoBlue® solution, metabolized by living cells changes the staining from blue to red. The absorbance is measured using a Victor3 multifunction spectrophotometer (Perkin Elmer, Turku, Finland) at a wavelength of 570 nm. The obtained results and represented in the graph correspond to the mean±SE of independent experiments performed in triplicate.

The HepG2 cell line was subjected to treatment with increasing concentrations (25-100 μg/mL) of both enantiomers of the B4a and B4b molecules. Linezolid is used as a reference molecule only to a final concentration of 100 micrograms/mL. Moreover, as an additional control, cells are also treated with 0.9% DMSO, used as a solvent of the substances.

Figure 5:
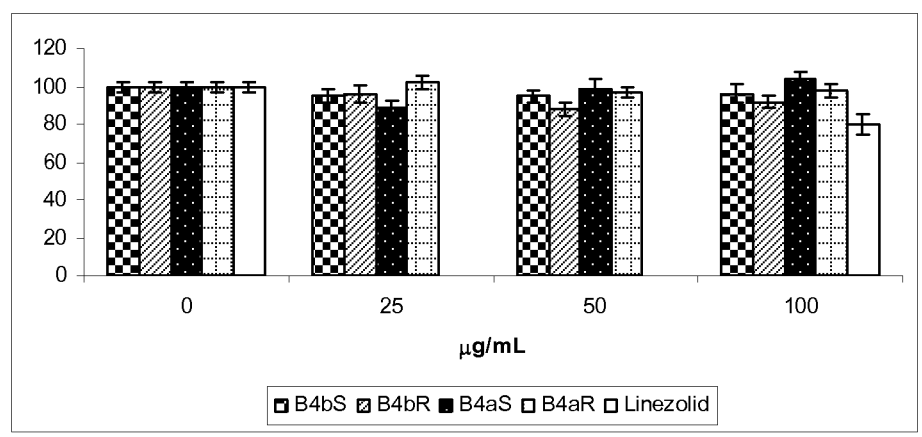
FIG. 5. Results of cell viability on HepG2 cells treated with B4a and B4b compounds (compounds 106 and 107 of Table 1) in the form of their respective enantiomers.
Figure 6:
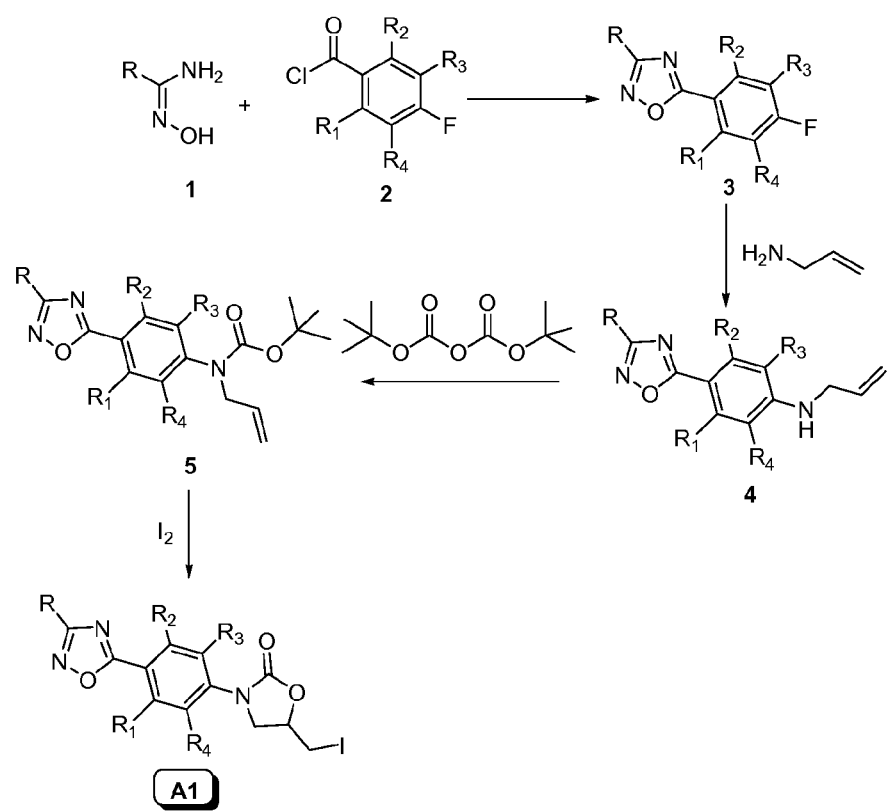
FIG. 6: Scheme 1 of chemical synthesis of compounds I-5 and A1
Figure 7:
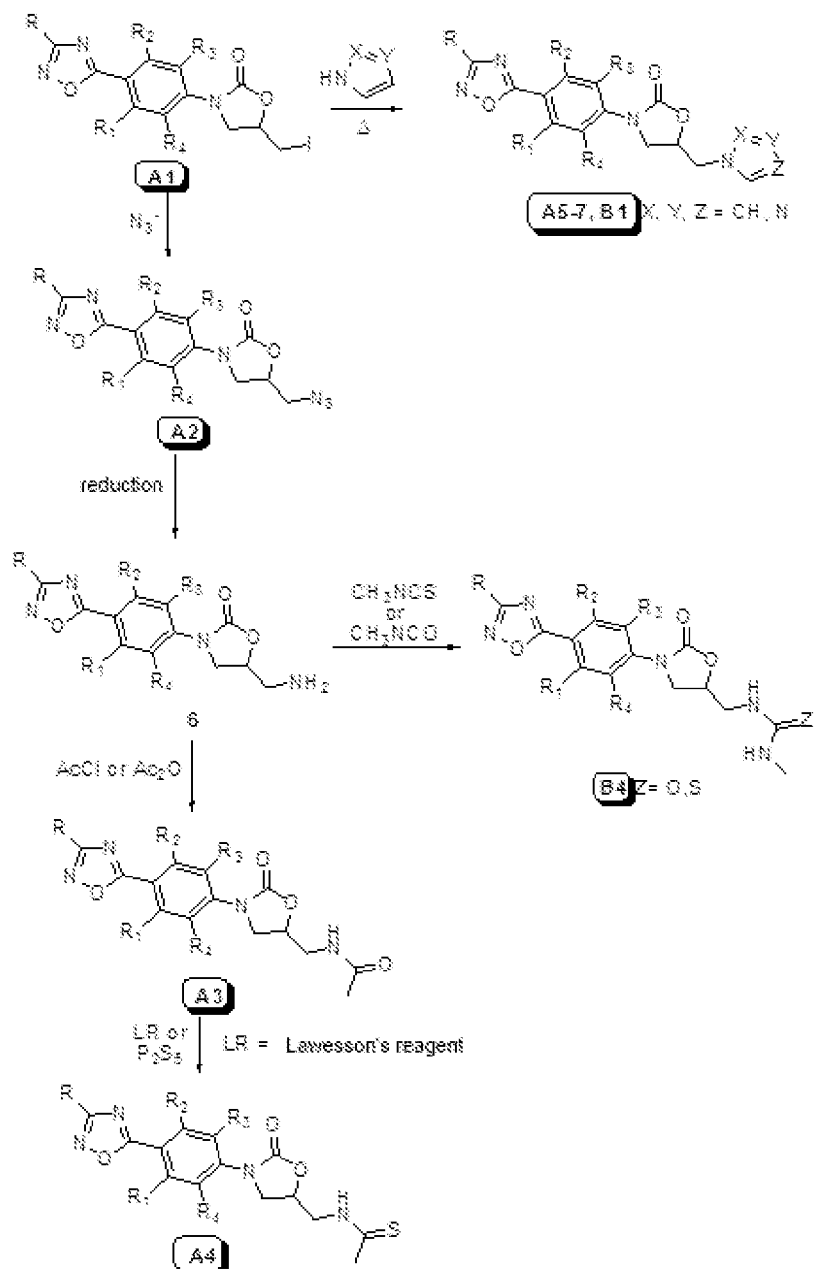
FIG. 7: Scheme 2 of chemical synthesis of A and B compounds
Figure 8:
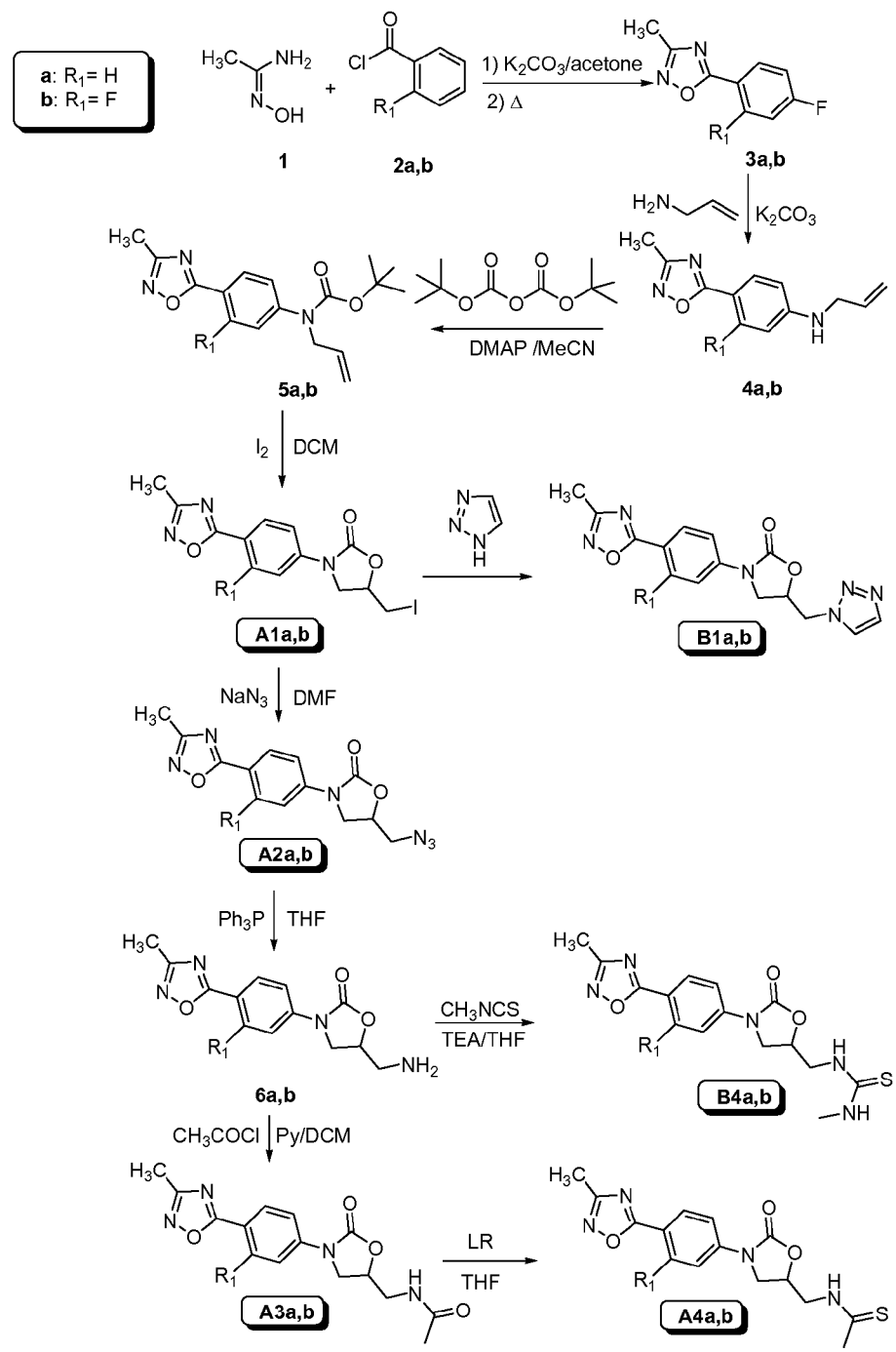
FIG. 8: Scheme 3 of chemical synthesis of the compounds of interest A and B.

Both enantiomers of the B4b molecule have induced a moderate reduction of viability (≤of 12%) in the HepG2 cell line at all the tested concentrations (FIG. 5). The S enantiomer of the B4a molecule has a slight concentration-independent cytotoxic effect in HepG2 cells (evident only at 25 micrograms/mL), while the R-enantiomer does not determine an apparent reduction in cell viability. HepG2 cells, as expected, is subject to a mortality of 20% after treatment with 100 micrograms/mL of linezolid.

Chemical Synthesis

Melting points were determined on a Reichart-Thermovar hotstage apparatus and are uncorrected. IR spectra (Nujol) were determined with a Shimadzu FTIR-8300 instrument; ¹H NMR spectra were recorded on a Bruker 300 Avance spectrometer using TMS as an internal standard. Flash chromatography was performed by using silica gel (0.040-0.063 mm) and mixtures of ethyl acetate and petroleum ether (fraction boiling in the range of 40-60° C.) in various ratios. The purity of compounds, in all cases higher than 95%, has been checked by both NMR and HPLC analyses. Separation of racemates was performed by means of HPLC with chiral stationary phase (Daicel, Chiralpak-IA), by using hexane-iPrOH (70:30) as mobile phase, and 1 mL/min flux. In every case an ee>99% was obtained.

The most interesting compounds:

A1a (compound 148 table 1), A1b (compound 149 table 1), A3a (compound 15 table 1), A3b (compound 16 table 1), A4a (compound 22 table 1), A4b (compound 23 table 1), B1a (compound 155 table 1), B1b (compound 156 table 1), B4a (compound 106 table 1), B4b (compound 107 table 1); reported in table 2 (group A) and 3 (group B) and corresponding intermediates 1-6, were obtained accordingly to general methodologies reported on schemes 1 and 2, following specifications indicated below and on scheme 3.

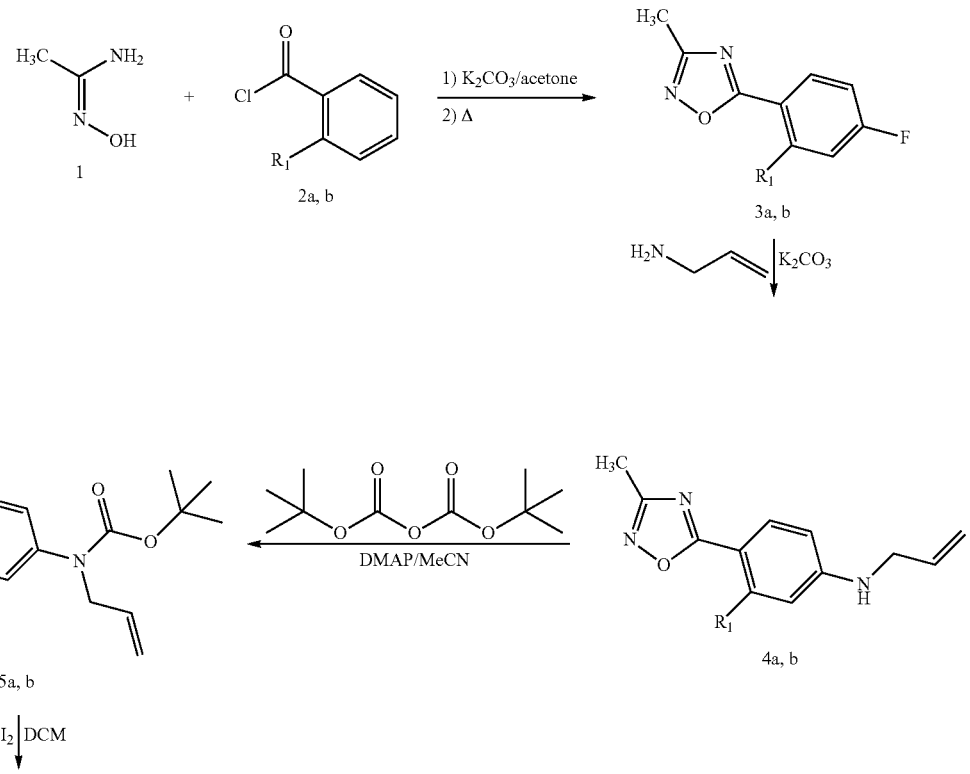

Scheme 3

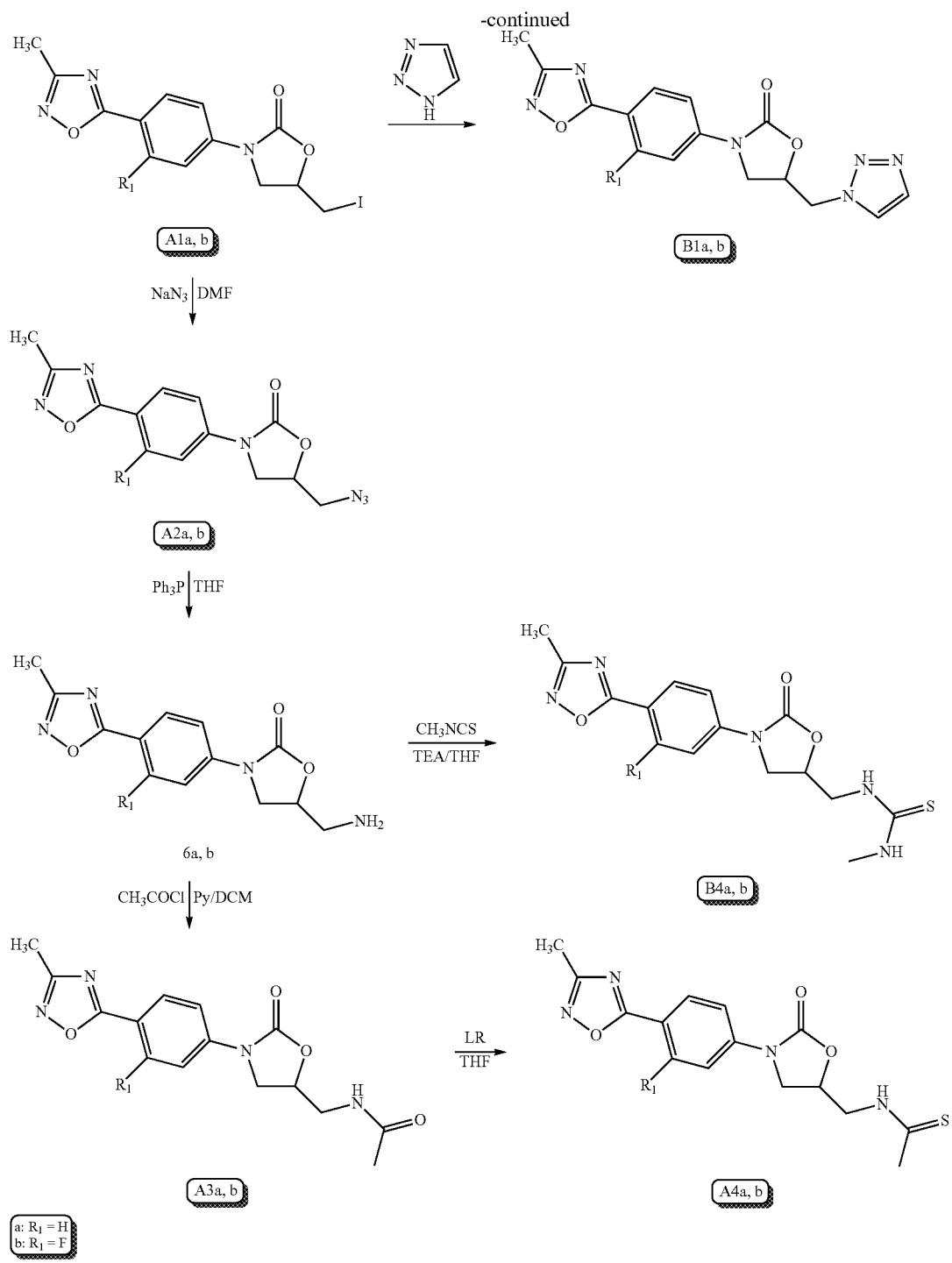

a: R₁ = H
b: R₁ = F

General Procedure for the Preparation of Compounds 3a,b

A solution of hydroxylamine hydrochloride (1.00 g, 14.4 mmol) and NaOH (0.57 g, 14.4 mmol) in water (5 mL) was added (in about 15 minutes) to 15 mL of CH₃CN. The reaction mixture was stirred at room temperature for 24 hours. The solvent was removed under reduced pressure and the residue treated with ethanol; the resulting suspension was filtered and the solvent was removed under reduced pressure producing 1.659 g of acetamidoxime 1 (77%). Then, either 4-fluorobenzoyl (2a) chloride or 2,4-difluorobenzoyl chloride (2b) (14.8 mmol) were added to a solution of 1 (1.00 g; 13.5 mmol) in Acetone (35 mL) containing also K₂CO₃ (2.05 g, 14.8 mmol). The mixture was stirred at room temperature for about 90 minutes after which the solvent was removed under reduced pressure. The residue was treated with water and the solid precipitate was collected by filtration. The obtained O-acylamidoxime was heated, without any further purification, at about 130° C. for 90 minutes in a sealed tube. The obtained residue was chromatographed yielding the corresponding 1,2,4-oxadiazoles 3a and 3b.

3-methyl-5-(4'-fluorophenyl)-1,2,4-oxadiazole (3a): Yield (72%); mp 80.0-81.0° C.; $^1$H NMR (300 MHz; CDCl$_3$) δ 2.45 (s, 3H, Me); 7.16-7.23 (m, 2H, Ar); 8.08-8.14 (m, 2H, Ar). Anal. Found (calc) for C$_9$H$_7$FN$_2$O (%): C, 60.65 (60.67); H, 3.90 (3.96); N, 15.70 (15.72).

3-methyl-5-(2',4'-difluorophenyl)-1,2,4-oxadiazole (3b): Yield (72%); mp 57.0-60.0° C.; $^1$H-NMR (300 MHz; CDCl$_3$) δ 2.46 (s, 3H, Me); 6.95-7.07 (m, 2H, Ar); 8.04-8.14 (m, 1H, Ar). Anal. Found (calc) for C$_9$H$_6$F$_2$N$_2$O (%): C, 55.15 (55.11); H, 3.10 (3.08); N, 14.25 (14.28).

Preparation of N-allyl-4-(3'-methyl-1,2,4-oxadiazol-5'-yl)-aniline (4a)

Compound 3a (0.61 g; 3.43 mmol) was heated, with allylamine (3.0 mL; 2.28 g; 40.0 mmol) and K$_2$CO$_3$ (2.00 g; 14.5 mmol), at about 60° C. for 8 days. The reaction mixture was treated with water and extracted with EtOAc. The organic layers were collected, dried over anhydrous Na$_2$SO$_4$, filtered and the solvent removed. The residue was chromatographed yielding compound 3a: Yield (54%); mp 63.9-65.5° C.; IR (Nujol) 3335 (NH), 1607 (C=N) cm$^{-1}$; $^1$H-NMR (300 MHz; DMSO-d$_6$) δ 2.31 (s, 3H, Me); 3.76-3.79 (m, 2H, CH$_2$); 5.12 (dd, 1H, J$_1$=10.5 Hz, J$_2$=1.8 Hz, —CH=CH$_2$); 5.22 (dd, 1H, J$_1$=17.1 Hz, J$_2$=1.8 Hz, —CH=CH$_2$); 5.82-5.93 (m, 1H, —CH=CH$_2$); 6.68 (d, 2H, J=9.0 Hz, Ar); 6.87 (t, 1H, J=5.7 Hz, NH, exch. with D$_2$O); 7.76 (d, 2H, J=9.0 Hz, Ar). Anal. Found (calc) for C$_{12}$H$_{13}$N$_3$O (%): C, 66.95 (66.96); H, 6.10 (6.09); N, 19.45 (19.52).

Preparation of N-allyl-3-fluoro-4-(3'-methyl-1,2,4-oxadiazol-5'-yl)aniline (4b)

To a solution of 3b (0.86 g; 4.38 mmol) in DMF (2.0 mL) was added allylamine (1.64 mL; 1.25 g; 22.0 mmol). The reaction mixture was stirred for 2 days, after which the solution was treated with water and extracted with EtOAc. The organic layers were collected, dried over anhydrous Na$_2$SO$_4$, filtered and the solvent removed. The residue was chromatographed yielding compound 4b: Yield (49%); mp 57.9-59.9° C.; IR (Nujol) 3335 (NH), 1626 (C=N) cm$^{-1}$; $^1$H-NMR (300 MHz; DMSO-d$_6$) δ 2.34 (s, 3H, Me); 3.77-3.81 (m, 2H, CH$_2$); 5.13 (dd, 1H, J$_1$=13.2 Hz, J$_2$=1.2 Hz, —CH=CH$_2$); 5.23 (dd, 1H, J$_1$=17.4 Hz, J$_2$=1.2 Hz, —CH=CH$_2$); 5.81-5.93 (m, 1H, —CH=CH$_2$); 6.46 (dd, 1H, J$_1$=14.4 Hz, J$_2$=1.8 Hz, Ar); 6.56 (dd, 1H, J$_1$=8.7 Hz, J$_2$=1.8 Hz, Ar); 7.17-7.21 (bs, 1H, NH, exch. with D$_2$O); 7.72-7.77 (m, 1H, Ar). Anal. Found (calc) for C$_{12}$H$_{12}$FN$_3$O (%): C, 61.80 (61.79); H, 5.10 (5.19); N, 18.15 (18.02).

General Procedure for the Preparation of Compounds 5a,b

Either compound 4a or 4b (2.15 mmol) were dissolved in CH$_3$CN (25 mL); di-(t-butyl)-dicarbonate (0.51 g; 2.36 mmol) and 4-dimethylaminopyridine (0.29 g; 2.36 mmol) were added and the mixture was stirred for 2 days or 2.5 hours, respectively. The solvent was removed under reduced pressure and the obtained residue was chromatographed yielding the corresponding compounds 5a and 5b.

tert-butyl N-allyl-(4-(3'-methyl-1,2,4-oxadiazol-5'-yl)-phenyl)-carbamate (5a): oil; Yield (73%); IR (Nujol) 1711 (NCO$_2$), 1614 (C=N) cm$^{-1}$; $^1$H-NMR (300 MHz; CDCl$_3$) δ 1.27 (s, 9H, t-Bu); 2.25 (s, 3H, Me); 4.10 (d, 2H, J=5.1 Hz, CH$_2$); 4.95-4.97 (m, 1H, —CH=CH$_2$); 4.99-5.01 (m, 1H, —CH=CH$_2$); 5.67-5.78 (m, 1H, —CH=CH$_2$); 7.23 (d, 2H, J=9.0 Hz, Ar); 7.84 (d, 2H, J=9.0 Hz, Ar). Anal. Found (calc) for C$_{17}$H$_{21}$N$_3$O$_3$ (%): C, 64.70 (64.74); H, 6.80 (6.71); N, 13.35 (13.32).

tert-butyl N-allyl-(3-fluoro-4-(3'-methyl-1,2,4-oxadiazol-5'-yl)-phenyl)-carbamate (5b): oil; Yield (72%); IR (Nujol) 1713 (NCO$_2$), 1615 (C=N) cm$^{-1}$; $^1$H-NMR (300 MHz; CDCl$_3$) δ 1.53 (s, 9H, t-Bu); 2.53 (s, 3H, Me); 4.36 (d, 2H, J=5.1 Hz, CH$_2$); 5.21-5.28 (m, 2H, —CH=CH$_2$); 5.91-6.02 (m, 1H, —CH=CH$_2$); 7.28-7.36 (m, 2H, Ar); 8.02-8.08 (m, 1H, Ar). Anal. Found (calc) for C$_{17}$H$_{20}$FN$_3$O$_3$ (%): C, 61.25 (61.25); H, 6.10 (6.05); N, 12.65 (12.61).

General Procedure for the Preparation of Compounds A1a,b

To a solution of 1.70 mmol of either compound 5a or 5b in CH$_2$Cl$_2$ (10 mL) was added I$_2$ sublimate (1.29 g; 5.10 mmol). The solution was stirred for 24 hours, after which the reaction was treated with a solution of Na$_2$SO$_3$; the organic layer was dried over anhydrous Na$_2$SO$_4$, filtered and the solvent removed. The residue was chromatographed yielding the corresponding compounds A1a and A1b.

3-(4'-(3"-methyl-1,2,4-oxadiazol-5"-yl)-phenyl)-5-(iodomethyl)-oxazolidin-2-one (A1a): Yield (89%); mp 145.0-147.0° C.; IR (Nujol) 1763 (NCO$_2$), 1618 (C=N) cm$^{-1}$; $^1$H-NMR (300 MHz; DMSO-d$_6$) δ 2.47 (s, 3H, Me); 3.62-3.73 (m, 2H, CH$_2$—I); 3.80 (dd, 1H, J$_1$=9.3 Hz, J$_2$=6.0 Hz, C$_4$—H); 4.34 (dd, 1H, J$_1$=9.3 Hz, J$_2$=9.0 Hz, C$_4$—H); 4.81-4.90 (m, 1H, C$_5$—H); 7.88 (d, 2H, J=9.0 Hz, Ar); 8.17 (d, 2H, J=9.0 Hz, Ar). Anal. Found (calc) for C$_{13}$H$_{12}$IN$_3$O$_3$ (%): C, 40.55 (40.54); H, 3.15 (3.14); N, 10.85 (10.91).

3-(3'-fluoro-4'-(3"-methyl-1,2,4-oxadiazol-5"-yl)-phenyl)-5-(iodomethyl)-oxazolidin-2-one (A1b): Yield (76%); mp 148.0-149.0° C.; IR (Nujol) 1743 (NCO$_2$), 1637 (C=N) cm$^{-1}$; $^1$H-NMR (300 MHz; DMSO-d$_6$) δ 2.48 (s, 3H, Me); 3.61-3.72 (m, 2H, CH$_2$—I); 3.81 (dd, 1H, J$_1$=9.6 Hz, J$_2$=6.0 Hz, C$_4$—H); 4.33 (dd, 1H, J$_1$=9.6 Hz, J$_2$=9.0 Hz, C$_4$—H); 4.83-4.93 (m, 1H, C$_5$—H); 7.68 (dd, 1H, J$_1$=8.7 Hz, J$_2$=2.1 Hz, Ar); 7.80 (dd, 1H, J$_1$=13.8 Hz, J$_2$=2.1 Hz, Ar); 8.16 (dd, 1H, J$_1$=8.7 Hz, J$_2$=8.5 Hz, Ar). Anal. Found (calc) for C$_{13}$H$_{11}$FIN$_3$O$_3$ (%): C, 38.75 (38.73); H, 2.55 (2.75); N, 10.35 (10.42).

General Procedure for the Preparation of Compounds A2a,b

To a solution of 0.75 mmol of compound A1a or A1b in DMF (6 mL) was added NaN$_3$ (0.39 g; 6.00 mmol). The solution was stirred for 24 hours, after which the reaction was treated with water and extracted with EtOAc; the organic layers were dried over anhydrous Na$_2$SO$_4$, filtered and the solvent removed. The residue was chromatographed yielding the corresponding compounds A2a and A2b.

3-(4'-(3"-methyl-1,2,4-oxadiazol-5-yl)-phenyl)-5-(azidometil)-oxazolidin-2-one (A2a): Yield (94%); mp 133.9-135.0° C.; IR (Nujol) 2095 (N$_3$), 1765 (NCO$_2$), 1727 (NCO$_2$), 1618 (C=N) cm$^{-1}$; $^1$H-NMR (300 MHz; DMSO-d$_6$) δ 2.46 (s, 3H, Me); 3.75-3.88 (m, 2H, CH$_2$—N$_3$); 3.92 (dd, 1H, J$_1$=9.3 Hz, J$_2$=6.0 Hz, C$_4$—H); 4.28 (t, 1H, J=9.3 Hz, C$_4$—H); 4.96-5.03 (m, 1H, C$_5$—H); 7.86 (d, 2H, J=9.0 Hz, Ar); 8.16 (d, 2H, J=9.0 Hz, Ar). Anal. Found (calc) for C$_{13}$H$_{12}$N$_6$C$_3$ (%): C, 52.05 (52.00); H, 4.10 (4.03); N, 27.85 (27.99).

3-(3'-fluoro-4'-(3"-methyl-1,2,4-oxadiazol-5-yl)-phenyl)-5-(azidometil)-oxazolidin-2-one (A2b): Yield (99%); mp 126.2-127.7° C.; IR (Nujol) 2107 (N$_3$), 1758 (NCO$_2$), 1743 (NCO$_2$), 1630 (C=N) cm$^{-1}$; $^1$H-NMR (300 MHz; DMSO-d$_6$) δ 2.41 (s, 3H, Me); 3.69-3.82 (m, 2H, CH$_2$—N$_3$); 3.86 (dd, 1H, J$_1$=9.3 Hz, J$_2$=6.0 Hz, C$_4$—H); 4.21 (t, 1H, J=9.3 Hz, C$_4$—H); 4.91-4.99 (m, 1H, C$_6$—H); 7.60 (dd, 1H, $J_1$=9.0 Hz, $J_2$=1.8 Hz, Ar); 7.72 (dd, 1H, $J_1$=13.5 Hz, $J_2$=1.8 Hz, Ar); 8.08-8.14 (m, 1H, Ar). Anal. Found (calc) for $C_{13}H_{11}FN_6O_3$ (%): C, 49.10 (49.06); H, 3.50 (3.48); N, 26.45 (26.41).

General Procedure for the Preparation of Compounds 6a,b

To a solution of 0.45 mmol of compound A2a or A2b in THF (15 mL) was added $PPh_3$ (0.16 g; 0.60 mmol). The solution was stirred for about 90 minutes, after which 100 µl of distilled water was added and the resulting mixture was refluxed for 4 hours. The THF was removed under reduced pressure, the resulting residue was neutralized with hydrochloric acid and extracted with EtOAc. A solution of NaOH (pH~9) was added to the aqueous phase, which was extracted with EtOAc; the organic layers were dried over anhydrous $Na_2SO_4$, filtered and the solvent removed, yielding the corresponding compounds 6a and 6b.

3-(4'-(3"-methyl-1,2,4-oxadiazol-5-yl)-phenyl)-5-(aminomethyl)-oxazolidin-2-one (6a): Yield (66%); mp 139.3-141.3° C.; IR (Nujol) 3390 (NH), 3361 (NH), 1748 ($NCO_2$), 1616 (C=N) $cm^{-1}$; $^1$H-NMR (300 MHz; DMSO-$d_6$) δ 2.22 (bs, 2H, $NH_2$, exch. with $D_2O$); 2.39 (s, 3H, Me); 2.77-2.91 (m, 2H, $CH_2$—$NH_2$); 3.94 (dd, 1H, $J_1$=9.0 Hz, $J_2$=6.3 Hz, $C_4$—H); 4.13 (t, 1H, J=9.0 Hz, $C_4$—H); 4.61-4.70 (m, 1H, $C_5$—H); 7.80 (d, 2H, J=9.0 Hz, Ar); 8.09 (d, 2H, J=9.0 Hz, Ar). Anal. Found (calc) for $C_{13}H_{14}N_4O_3$ (%): C, 56.90 (56.93); H, 5.15 (5.14); N, 20.45 (20.43).

3-(3'-fluoro-4'-(3"-methyl-1,2,4-oxadiazol-5-yl)-phenyl)-5-(aminomethyl)-oxazolidin-2-one (6b): Yield (88%); mp 137.0-140.0° C.; IR (Nujol) 3372 (NH), 1743 ($NCO_2$), 1630 (C=N) $cm^{-1}$; $^1$H-NMR (300 MHz; DMSO-$d_6$) δ 2.21 (bs, 2H, $NH_2$, exch. with $D_2O$); 2.41 (s, 3H, Me); 2.77-2.91 (m, 2H, $CH_2$—$NH_2$); 3.93 (dd, 1H, $J_1$=9.3 Hz, $J_2$=6.3 Hz, $C_4$—H); 4.13 (t, 1H, J=9.0 Hz, $C_4$—H); 4.63-4.71 (m, 1H, $C_6$—H); 7.60 (dd, 1H, $J_1$=9.0 Hz, $J_2$=2.1 Hz, Ar); 7.73 (dd, 1H, $J_1$=10.8 Hz, $J_2$=2.1 Hz, Ar); 8.08-8.14 (m, 1H, Ar). Anal. Found (calc) for $C_{13}H_{13}FN_4O_3$ (%): C, 53.40 (53.42); H, 4.45 (4.48); N, 19.25 (19.17).

General Procedure for the Preparation of Compounds A3a,b

Acetyl chloride (40 µl; 44 mg; 0.56 mmol) was added to a solution of either compound A3a or A3b (0.28 mmol) in $CH_2Cl_2$ (3 mL) containing also pyridine (1 mL; 0.97 g; 12.3 mmol). The solution was stirred for 30 minutes after which the solvent was removed and the residue treated with HCl 1M (20 mL) and extracted with EtOAc; the organic layers were dried over anhydrous $Na_2SO_4$, filtered and the solvent removed. The residue was chromatographed yielding the corresponding compounds A3a and A3b.

3-(4'-(3"-methyl-1,2,4-oxadiazol-5-yl)-phenyl)-5-(N-acetylaminomethyl)-oxazolidin-2-one (A3a): Yield (58%); mp 214.0-216.0° C.; IR (Nujol) 3257 (NH), 1751 ($NCO_2$), 1646 (amide), 1616 (C=N) $cm^{-1}$; $^1$H-NMR (300 MHz; DMSO-$d_6$) δ 1.89 (s, 3H, COMe); 2.46 (s, 3H, Me); 3.50 (t, 2H, J=5.7 Hz, $CH_2$—NHCOMe); 3.88 (dd, 1H, $J_1$=9.0 Hz, $J_2$=6.6 Hz, $C_4$—H); 4.25 (t, 1H, J=9.0 Hz, $C_4$—H); 4.79-4.87 (m, 1H, $C_5$—H); 7.84 (d, 2H, J=8.7 Hz, Ar); 8.16 (d, 2H, J=8.7 Hz, Ar); 8.32 (t, 1H, J=5.7 Hz, NH, exch. with $D_2O$); $^{13}$C-NMR (75 MHz; DMSO-$d_6$) δ 11.4, 22.6, 41.5, 47.2, 72.0, 118.1 (overlapped signals), 128.9, 142.6, 154.1, 167.7, 170.2, 174.5. Anal. Found (calc) for $C_{15}H_{16}N_4O_4$ (%): C, 56.95 (56.96); H, 5.05 (5.10); N, 17.85 (17.71).

3-(3'-fluoro-4'-(3"-methyl-1,2,4-oxadiazol-5-yl)-phenyl)-5-(N-acetylaminomethyl)-oxazolidin-2-one (A3b): Yield (62%); mp 184.0-186.0° C.; IR (Nujol) 3343 (NH), 1751 ($NCO_2$), 1666 (amide), 1628 (C=N) $cm^{-1}$; $^1$H-NMR (300 MHz; DMSO-$d_6$) δ 1.89 (s, 3H, COMe); 2.48 (s, 3H, Me); 3.50 (t, 2H, J=5.4 Hz, $CH_2$—NHCOMe); 3.88 (dd, 1H, $J_1$=9.3 Hz, $J_2$=6.3 Hz, $O_4$—H); 4.25 (t, 1H, J=9.0 Hz, $O_4$—H); 4.81-4.88 (m, 1H, $O_5$—H); 7.64 (dd, 1H, $J_1$=9.0 Hz, $J_2$=1.8 Hz, Ar); 7.77 (dd, 1H, $J_1$=13.8 Hz, $J_2$=1.8 Hz, Ar); 8.15-8.21 (m, 1H, Ar), 8.31 (m, 1H, NH, exch. with $D_2O$); $^{13}$C-NMR (75 MHz; DMSO-$d_6$) δ 11.32, 22.6, 41.5, 47.3, 72.2, 105.7 (d, $J_{C-F}$=32 Hz), 106.2 (d, $J_{C-F}$=14 Hz), 114.1, 131.4, 144.3 (d, $J_{C-F}$=14 Hz), 153.9, 160.4 (d, $J_{C-F}$=305 Hz), 167.5, 170.2, 171.6. Anal. Found (calc) for $C_{15}H_{15}FN_4O_4$ (%): C, 53.90 (53.89); H, 4.65 (4.52); N, 16.65 (16.76).

General Procedure for the Preparation of Compounds A4a,b

The Lawesson's reagent (0.2 g; 0.49 mmol) was added to a solution of either A3a or A3b (0.49 mmol) in THF (14 mL). The reaction mixture was refluxed for 2 hours, after which the solvent was removed under reduced pressure. The residue was chromatographed yielding the corresponding compounds A4a and A4b.

3-(4'-(3"-methyl-1,2,4-oxadiazol-5-yl)-phenyl)-5-(N-thioacetylaminomethyl)-oxazolidin-2-one (A4a): Yield (77%); mp 199.4-201.0° C.; IR (Nujol) 3217 (NH), 1721 ($NCO_2$), 1618 (thioamide) $cm^{-1}$; $^1$H-NMR (300 MHz; DMSO-$d_6$) δ 2.47 (s, 3H, Me); 2.51 (s, 3H, CSMe); 3.95-4.03 (m, 3H, overlapped signals); 4.28-4.34 (m, 1H, $C_4$—H); 5.01-5.11 (m, 1H, $C_5$—H); 7.85 (d, 2H, J=9.0 Hz, Ar); 8.18 (d, 2H, J=9.0 Hz, Ar); 10.45 (bs, 1H, NH, exch. with $D_2O$). Anal. Found (calc) for $C_{15}H_{16}N_4O_3S$ (%): C, 54.15 (54.20); H, 4.85 (4.85); N, 16.90 (16.86).

3-(3'-fluoro-4'-(3"-methyl-1,2,4-oxadiazol-5-yl)-phenyl)-5-(N-thioacetylaminomethyl)-oxazolidin-2-one (A4b): Yield (93%); mp 166.5-167.7° C.; IR (Nujol) 3262 (NH), 1746 ($NCO_2$), 1633 (thioamide) $cm^{-1}$; $^1$H-NMR (300 MHz; DMSO-$d_6$) δ 2.48 (s, 3H, Me); 2.51 (s, 3H, CSMe); 3.94-4.00 (m, 3H, overlapped signals); 4.28-4.34 (m, 1H, $C_4$—H); 5.04-5.12 (m, 1H, $C_5$—H); 7.65 (dd, 1H, $J_1$=9 Hz, $J_2$=1.8 Hz, Ar); 7.78 (dd, 1H, $J_1$=13.5 Hz, $J_2$=1.8 Hz, Ar); 8.16-8.22 (m, 1H, Ar); 10.45 (bs, 1H, NH exch. with $D_2O$). Anal. Found (calc) for $C_{15}H_{14}FN_4O_3S$ (%): C, 51.35 (51.42); H, 4.30 (4.32); N, 16.05 (15.99).

General Procedure for the Preparation of Compounds B1a,b

In a glass tube, to 0.45 mmol of compound A1a or A1b was added 1,2,3-triazole (0.124 g; 1.8 mmol). The mixture was heated until complete consumption of the starting material monitored by TLC. The residue was chromatographed yielding the corresponding compounds B1a and B1b.

((3-(4-(3-methyl-1,2,4-oxadiazol-5-yl)phenyl)-oxazolidin-2-on-5-yl)methyl)-4,5-dihydro-1H-1,2,3-triazole (B1a): Yield (73%); mp 208-210° C.; IR (Nujol) v 1751 $cm^{-1}$; $^1$H-NMR (300 MHz; $CDCl_3$) δ 2.46 (s, 3H), 4.03 (dd, $J_1$=6.3 Hz, $J_2$=9.3 Hz, 1H), 4.25 (dd, $J_1$=9.3 Hz, $J_2$=9.0 Hz, 1H), 4.82-4.83 (m, 2H), 5.08-5.14 (m, 1H), 7.59 (d, J=9.0 Hz, 1H), 7.75 (s, 1H), 7.80 (s, 1H), 8.08 (d, J=9.0 Hz, 1H); Anal. Found (calc) for $C_{15}H_{14}N_6O_3$ (%): C, 55.30 (55.21); H, 4.39 (4.32); N, 25.69 (25.75).

((3-(3-fluoro-4-(3-methyl-1,2,4-oxadiazol-5-yl)phenyl)-oxazolidin-2-on-5-yl)methyl)-4,5-dihydro-1H-1,2,3-triazole (B1b): Yield (64%); mp 176.2-177.8° C.; IR (Nujol) v 1751 cm$^{-1}$; $^1$H-NMR (300 MHz; CDCl$_3$) δ 2.48 (s, 3H), 4.03 (dd, J$_1$=9.3 Hz, J$_2$=6.0 Hz, 1H), 4.25 (dd, J$_1$=9.6 Hz, J$_2$=9.0 Hz, 1H), 4.82-4.83 (m, 2H), 5.15-5.30 (m, 1H), 7.27 (dd, J$_1$=8.3 Hz, J$_2$=1.8 Hz, 1H), 7.56 (dd, J$_1$=12.6 Hz, J$_2$=1.8 Hz, 1H), 7.75 (s, 1H), 7.79 (s, 1H), 8.02 (t, J=8.3 Hz, 1H); Anal. Found (calc) for C$_{15}$H$_{13}$FN$_6$O$_3$ (%): C, 52.37 (52.33); H, 3.85 (3.81); N, 24.47 (24.41).

General Procedure for the Preparation of Compounds B4a,b

To a solution of 0.55 mmol of compound 6a or 6b in THF (5 mL) was added CH$_3$NCS (0.041 mL; 0.60 mmol) and triethylamine (0.084 mL; 0.60 mmol). The solution was stirred for 3 hours at room temperature. The solvent was then removed under vacuum. The residue was chromatographed yielding the corresponding compounds B4a and B4b.

1-((3-(4-(3-methyl-1,2,4-oxadiazol-5-yl)phenyl)-oxazolidin-2-one-5-yl)methyl)-3-methylthiourea (B4a): Yield (80%); mp 189.4-191.8° C.; IR (Nujol) v 3364, 1732 cm$^{-1}$; $^1$H-NMR (300 MHz; CDCl$_3$) δ 2.39 (s, 3H), 2.82 (bs, 3H), 3.82-4.00 (m, 3H), 4.20 (dd, J$_1$=8.7 Hz, J$_2$=6.0 Hz, 1H), 4.91 (bs, 1H), 7.77-7.80 (m, 3H), 8.09 (d, J=6.9 Hz, 2H); Anal. Found (calc) for C$_{15}$H$_{17}$N$_5$O$_3$S (%): C, 51.91 (51.86); H, 5.00 (4.93); N, 20.20 (20.16).

1-((3-(3-fluoro-4-(3-methyl-1,2,4-oxadiazol-5-yl)phenyl)-oxazolidin-2-one-5-yl)methyl)-3-methylthiourea (B4b): Yield (88%); mp 170.7-172.4° C.; IR (Nujol) v 3370, 1739 cm$^{-1}$; $^1$H-NMR (300 MHz, DMSO) δ 2.48 (s, 3H), 2.89 (bs, 3H), 3.89-4.07 (m, 3H), 4.24-4.30 (m, 1H), 4.89 (bs, 1H), 7.74 (s, 1H), 7.79 (dd, J$_1$=13.5 Hz, J$_2$=2.1 Hz, 2H), 8.20 (t, J=9.0 Hz, 2H); Anal. Found (calc) for C$_{15}$H$_{16}$FN$_5$O$_3$S (%): C, 49.21 (49.31); H, 4.35 (4.41); N, 19.10 (19.17).

REFERENCES

[1] S. Tsiodras, H. S. Gold, G. Sakoulas, G. M. Eliopoulos, C. Wennersten, L. Venkataraman, R. C. Moellering, M. J. Ferraro, *Lancet* 2001, 358, 207-208.
[2] C. Auckland, L. Teare, F. Cooke, M. E. Kaufmann, M. Warner, G. Jones, K. Bamford, H. Ayles, A. P. Johnson, *J. Antimicrob. Chemother.* 2002, 50, 743-746.
[3] J. Seedat, G. Zick, I. Klare, C. Konstabel, N. Weiler, H. Sahly, *Antimicrob. Ag. Chemother.* 2006, 50, 4217-4219.
[4] S. Kelly, J. Collins, M. Maguire, C. Gowing, M. Flanagan, M. Donnelly, P. G. Murphy, *J. Antimicrob. Chemother.* 2008, 61, 901-907.
[5] J. V. N. Vara Prasad, *Curr. Op. Microbiol.* 2007, 10, 454-460.
[6] C. Farrerons Gallemi, 2005, US Patent 2005/0014806.
[7] L. B. Snyder, Z. Meng, R. Mate, S. V. D'Andrea, A. Marinier, et al.; *Bioorg. Med. Chem. Lett.*, 2004, 14, 4735-4739.
[8] A. Palumbo Piccionello, R. Musumeci, C. Cocuzza, C. G. Fortuna, A. Guarcello, P. Pierro, A. Pace, *Eur. J. Med. Chem.* 2012, 50, 441-448.
[9] A. Pace, P. Pierro, *Org. Biomol. Chem.* 2009, 7, 4337-4348.
[10] S. Buscemi, A. Pace, R. Calabrese, N. Vivona, P. Metrangolo, *Tetrahedron* 2001, 57, 5865-5871.
[11] S. Buscemi, A. Pace, A. Palumbo Piccionello, I. Pibiri, N. Vivona, *Heterocycles* 2004, 63, 1619-1628.
[12] A. Palumbo Piccionello, A. Pace, I. Pibiri, S. Buscemi, N. Vivona, *Tetrahedron* 2006, 62, 8792-8797.
[13] A. Palumbo Piccionello, A. Pace, P. Pierro, I. Pibiri, S. Buscemi, N. Vivona, *Tetrahedron* 2009, 65, 119-127.
[14] K. C. Grega, M. R. Barbachyn, S. J. Brickner, S. A. Mizsak, *J. Org. Chem.* 1995, 60, 5255-5261.
[15] H. Biswajit Das, H. Sonali Rudra, A. Songita Songita, P. Mohammad Salman, H. Ashok Rattan, 2008, US Patent 2008/0188470.
[16] Clinical and Laboratory Standards Institute. Methods for Dilution Antimicrobial Susceptibility Tests for Bacteria That Grow Aerobically; Approved Standard—Ninth Edition. 2011, M07-A9, 32, Wayne, Pennsylvenia.
[17] E. C. Pirtle, *Am. J. Vet. Res.* 1966, 27, 747-749.
[18] D. P. Aden, A. Fogel, S. Plotkin, I. Damjanov, B. B. Knowles, *Nature* 1979, 282, 615-616.
[19] G. Pozzi, M. Guidi, F. Laudicina, M. Marazzi, L. Falcone, R. Betti, C. Crosti, E. Müller, G. E. Di Mattia, V. Locatelli, A. Torsello, *J. Endocrinol. Invest.* 2004, 27, 142-149.
[20] A. Bulbarelli, E. Lonati, E. Cazzaniga, M. Gregori, M. Masserini, *Mol. Cell. Neurosci.* 2009, 42, 75-80.

The invention claimed is:
1. A compound for treatment of an infection caused by Gram-positive bacteria, the compound being of general formula (II)

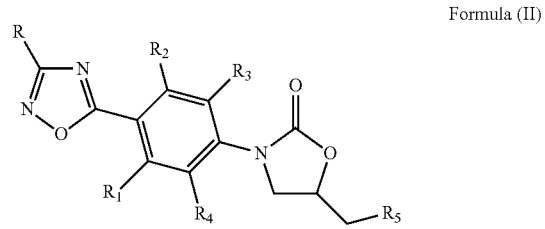

Formula (II)

as a racemic mixture or a pure enantiomer or a mixture enriched in either S or R enantiomer, wherein:
R=methyl or ethyl;
R$_{1-4}$=independently H or F or Cl or Br;
R$_5$=—NH$_2$; —OH; —NCS; —NHC(X)CH$_3$ with X=O or S; —NHC(X)CH$_2$Z with X=O or S, and Z=F or Cl; —NHC(X)CHZ$_2$ with X=O or S, and Z=F or Cl; —NHC(X)CZ$_3$ with X=O or S, and Z=F or Cl; or —NHC(X)NHR$_7$ with X=O or S, and R$_7$=H, C1-C3-alkyl, C3-C6-cyclo-alkyl, aryl, heteroaryl, C1-C3-acyl, or an N-substituted azole.

2. The compound as claimed in claim 1 wherein at least one of the R$_1$, R$_2$, R$_3$ or R$_4$ substituents is a fluorine atom, while the others are H.

3. The compound as claimed in claim 1 wherein R$_5$ is selected from the group consisting of —NHC(=O)CH$_3$, —NHC(=S)CH$_3$, —NHC(=O)CH$_2$F, —NHC(=S)CH$_2$F, —NHC(=O)CH$_2$Cl, —NHC(=S)CH$_2$Cl, —NHC(=S)NH$_2$, NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, and —NCS.

4. The compound as claimed in claim 1 selected from the group consisting of compounds wherein:
R$_5$ is —NHC(=S)CH$_3$ and R is CH$_3$;
R$_5$ is —NHC(=S)NHCH$_3$ and R is CH$_3$;
R$_5$ is —NHC(=O)CH$_3$ and R is CH$_3$; and
R$_5$ is —NHC(=S)NH$_2$ and R is CH$_3$.

5. The compound as claimed in claim 1 selected from the group consisting of compounds wherein:
R=CH$_3$; R$_1$=H; R$_2$=H; R$_3$=H; R$_4$=H; R$_5$=NHC(=O)CH$_3$;
R=CH$_3$; R$_1$=F; R$_2$=H; R$_3$=H; R$_4$=H; R$_5$=NHC(=O)CH$_3$;
R=CH$_3$; R$_1$=H; R$_2$=F; R$_3$=H; R$_4$=H; R$_5$=NHC(=O)CH$_3$;
R=CH$_3$; R$_1$=H; R$_2$=H; R$_3$=H; R$_4$=H; R$_5$=NHC(=S)CH$_3$;
R=CH$_3$; R$_1$=F; R$_2$=H; R$_3$=H; R$_4$=H; R$_5$=NHC(=S)CH$_3$;

R=CH$_3$; R$_1$=F; R$_2$=F; R$_3$=H; R$_4$=H; R$_5$=NHC(=O)CH$_3$S;

R=CH$_3$; R$_1$=H; R$_2$=H; R$_3$=H; R$_4$=H; R$_5$=NHC(=S)NHCH$_3$;

R=CH$_3$; R$_1$=F; R$_2$=H; R$_3$=H; R$_4$=H; R$_5$=NHC(=S)NHCH$_3$; and

R=CH$_3$; R$_1$=F; R$_2$=F; R$_3$=H; R$_4$=H; R$_5$=NHC(=S)NHCH$_3$.

6. The compound as claimed in claim 1 in the form of pure S enantiomer or mixture enriched with the S enantiomer.

7. The compound as claimed in claim 5 in the form of pure S enantiomer or mixture enriched with the S enantiomer.

8. A pharmaceutical composition for treatment of an infection caused by Gram-positive bacteria, containing a compound having general formula (II)

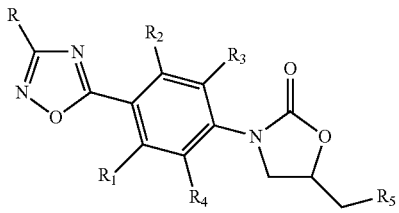

Formula (II)

as a racemic mixture or a pure enantiomer or a mixture enriched in either S or R enantiomer, wherein:
R=methyl or ethyl;
R$_{1-4}$=independently H or F or Cl or Br;
R$_5$=—NH$_2$; —OH; —NCS; —NHC(X)CH$_3$ with X=O or S; —NHC(X)CH$_2$Z with X=O or S, and Z=F or Cl; —NHC(X)CHZ$_2$ with X=O or S, and Z=F or Cl; —NHC(X)CZ$_3$ with X=O or S, and Z=F or Cl; or —NHC(X)NHR$_7$ with X=O or S, and R$_7$=H, C1-C3-alkyl, C3-C6-cyclo-alkyl, aryl, heteroaryl, C1-C3-acyl or an N-substituted azole;
and a pharmaceutically acceptable excipient.

9. A pharmaceutical composition according to claim 8 wherein at least one of the substituents R$_1$, R$_2$, R$_3$ or R$_4$ is a fluorine atom, while the others are H.

10. A pharmaceutical composition according to claim 8 wherein R$_5$ is selected from the group consisting of: NHC(=O)CH$_3$, NHC(=S)CH$_3$, —NHC(=O)CH$_2$F, —NHC(=S)CH$_2$F, —NHC(=O)CH$_2$Cl, —NHC(=S)CH$_2$Cl, —NHC(=S)NH$_2$, NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, and —NCS.

11. A pharmaceutical composition according to claim 8 containing a compound selected from the group consisting of compounds wherein:

R$_5$ is NHC(=S)CH$_3$ and R is CH$_3$;
R$_5$ is NHC(=S)NHCH$_3$ and R is CH$_3$;
R$_5$ is NHC(=O)CH$_3$ and R is CH$_3$; and
R$_5$ is NHC(=S)NH$_2$ and R is CH$_3$.

12. A pharmaceutical composition according to claim 8 wherein the compound is selected from the group consisting of compounds wherein:

R=CH$_3$; R$_1$=H; R$_2$=H; R$_3$=H; R$_4$=H; R$_5$=NHC(=O)CH$_3$;
R=CH$_3$; R$_1$=F; R$_2$=H; R$_3$=H; R$_4$=H; R$_5$=NHC(=O)CH$_3$;
R=CH$_3$; R$_1$=F; R$_2$=F; R$_3$=H; R$_4$=H; R$_5$=NHC(=O)CH$_3$;
R=CH$_3$; R$_1$=H; R$_2$=H; R$_3$=H; R$_4$=H; R$_5$=NHC(=S)CH$_3$;
R=CH$_3$; R$_1$=F; R$_2$=H; R$_3$=H; R$_4$=H; R$_5$=NHC(=S)CH$_3$;
R=CH$_3$; R$_1$=F; R$_2$=F; R$_3$=H; R$_4$=H; R$_5$=NHC(=O)CH$_3$S;
R=CH$_3$; R$_1$=H; R$_2$=H; R$_3$=H; R$_4$=H; R$_5$=NHC(=S)NHCH$_3$;
R=CH$_3$; R$_1$=F; R$_2$=H; R$_3$=H; R$_4$=H; R$_5$=NHC(=S)NHCH$_3$; and
R=CH$_3$; R$_1$=F; R$_2$=F; R$_3$=H; R$_4$=H; R$_5$=NHC(=S)NHCH$_3$.

13. A pharmaceutical composition according to claim 8 wherein the compound is in the form of S-enantiomer or a mixture enriched in S-enantiomer.

14. A pharmaceutical composition according to claim 12 wherein the compound is in the form of S-enantiomer or a mixture enriched in S-enantiomer.

15. A pharmaceutical composition according to claim 8 for oral use in the form of tablet, capsule, syrup, solution or for parenteral use in the form of aqueous or oily solution or emulsion, or for topical use in the form of ointment, cream, gel, solution, emulsion O/W or W/O suspension.

16. A pharmaceutical composition according to claim 12 for oral use in the form of tablet, capsule, syrup, solution or for parenteral use in the form of aqueous or oily solution or emulsion, or for topical use in the form of ointment, cream, gel, solution, emulsion O/W or W/O suspension.

17. A method of therapeutic treatment of infections by Gram-positive bacteria, optionally multi antibiotic-resistant, comprising administering to a patient a pharmaceutically active amount of a composition according to claim 8.

18. A method of therapeutic treatment of infections by Gram-positive bacteria, optionally multi antibiotic-resistant, comprising administering to a patient a pharmaceutically active amount of a composition according to claim 14.

19. Method of treatment according to claim 17 in the treatment of infections caused by *Staphylococcus* spp, *Enterococcus* spp, *Streptococcus* spp, optionally resistant to antibiotics.

20. Method of treatment according to claim 18 in the treatment of infections caused by *Staphylococcus* spp, *Enterococcus* spp, *Streptococcus* spp, optionally resistant to antibiotics.

21. Process for preparation of a compound according to claim 1 comprising:

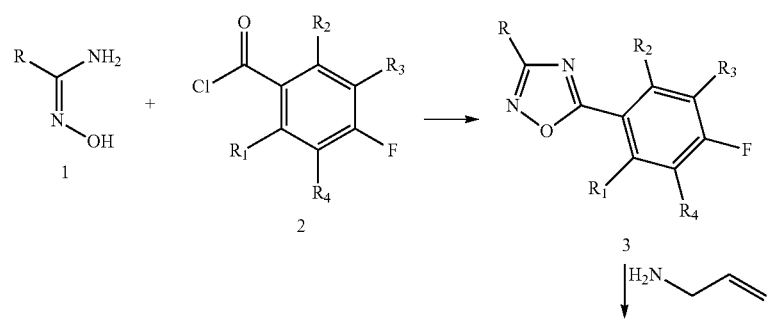

31 32
-continued
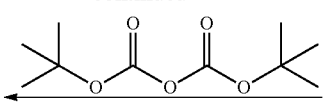
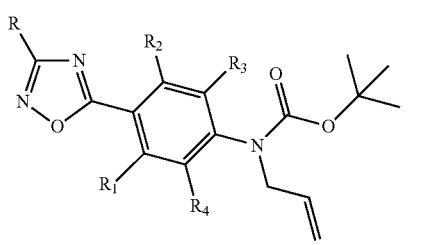
5
  I₂
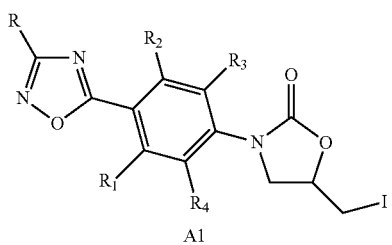
A1
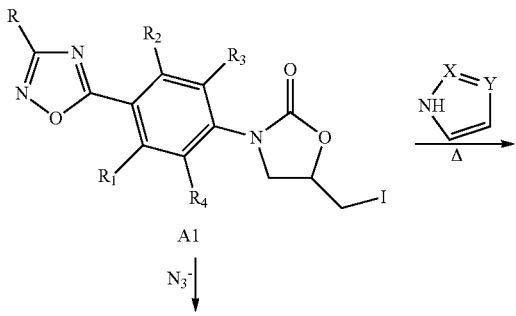
A1
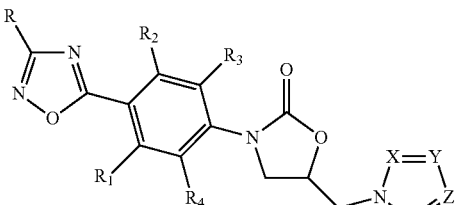
A5-7, B1  X, Y, Z = CH, N
  N₃⁻
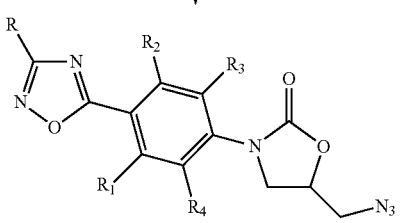
A2
reduction
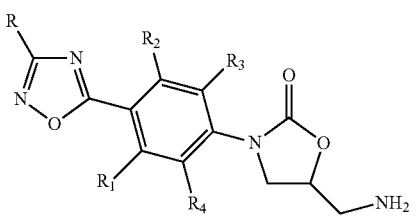
6
  AcCl or Ac₂O
CH₃NCS
or
CH₃NCO
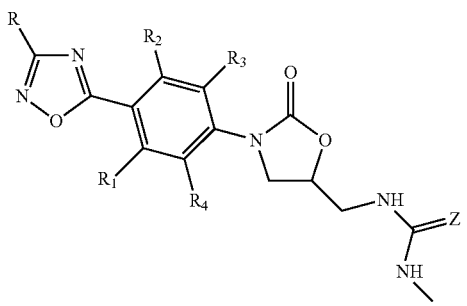
B4  Z = O, S

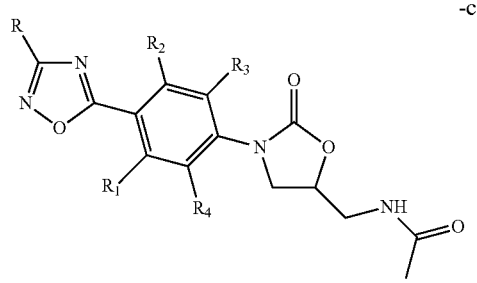

A3

LR or P₂S₅ | LR = Lawesson's Reagent

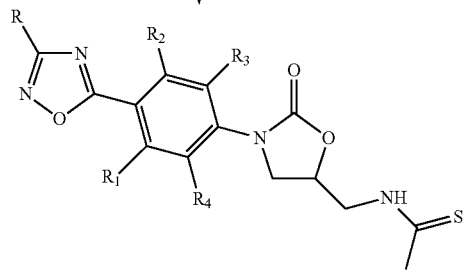

A4

(a) reacting amidoxime 1 with benzoyl chloride 2 to produce 1,2,4-oxadiazole 3;
(b) reacting 1,2,4-oxadiazole 3, having its para position activated to undergo aromatic nucleophilic substitution, with allylamine to yield compound 4;
(c) reacting, compound 4 with di-(t-butyl)-dicarbonate to obtain derivative 5;
(d) carrying out cyclization of derivative 5 to yield oxazolidinone A1;

Scheme 2

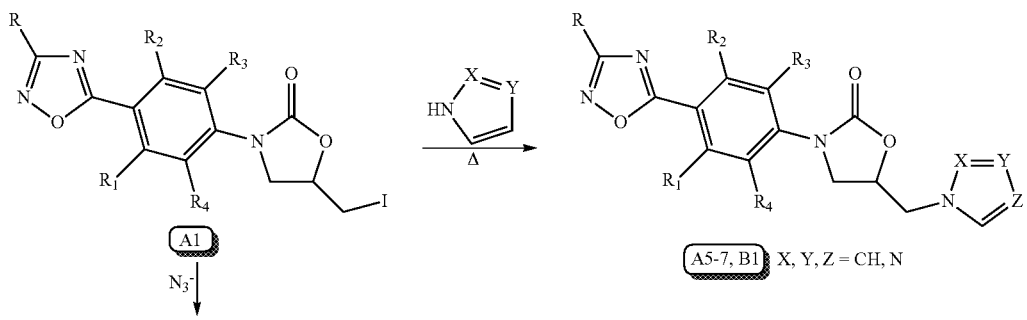

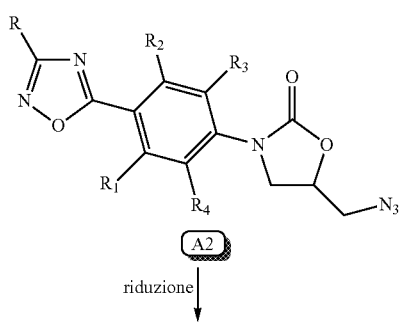

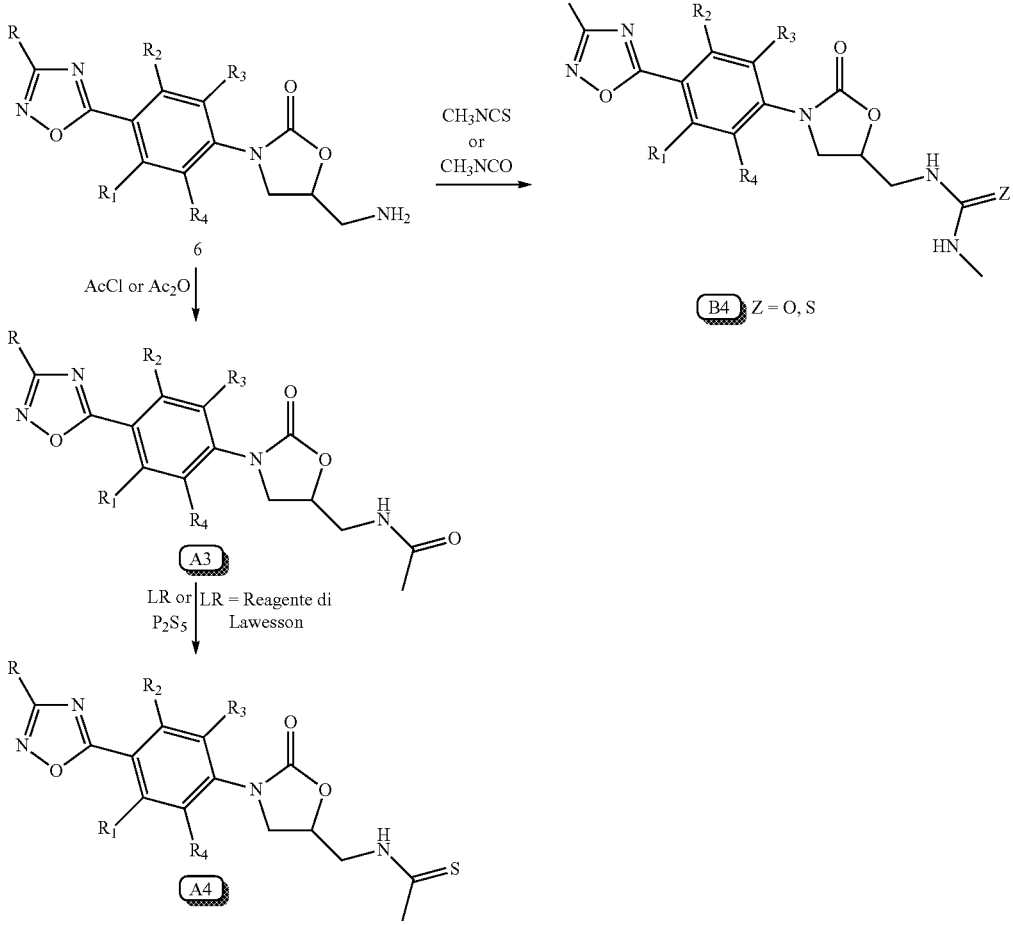

(e) reacting compound A1 with azide to obtain azide precursor A2, or carrying out nucleophilic substitution to obtain an azole derivative A5-7, B1;
(f) carrying out reduction of azide precursor A2 to yield amino derivative 6;
(g) reacting amino derivative 6 with acetyl chloride or acetic anhydride to obtain acetamidomethyl derivative A3, or with iso(thio)cyanate to obtain (thio)urea B4; and
(h) reacting acetamidomethyl derivative A3 with Lawesson's Reagent or $P_2S_5$ to yield thioamide derivative A4.

22. Process according to claim 21 further comprising separating enantiomers S and R or enriching a racemic mixture in one of the enantiomers.

23. The compound as claimed in claim 6 selected from the group consisting of compounds wherein:
$R=CH_3$; $R_1=H$; $R_2=H$; $R_3=H$; $R_4=H$; $R_5=NHC(=O)CH_3$;
$R=CH_3$; $R_1=F$; $R_2=H$; $R_3=H$; $R_4=H$; $R_5=NHC(=O)CH_3$;
$R=CH_3$; $R_1=F$; $R_2=H$; $R_3=H$; $R_4=H$; $R_5=NHC(=S)CH_3$; and
$R=CH_3$; $R_1=F$; $R_2=H$; $R_3=H$; $R_4=H$; $R_5=NHC(=S)NHCH_3$.

24. The compound as claimed in claim 1 wherein $R_5$ is 1,2,3-triazole.

25. A pharmaceutical composition according to claim 8 wherein $R_5$ is 1,2,3-triazole.

* * * * *